United States Patent
Derchak et al.

(10) Patent No.: US 7,762,953 B2
(45) Date of Patent: Jul. 27, 2010

(54) SYSTEMS AND METHODS FOR NON-INVASIVE PHYSIOLOGICAL MONITORING OF NON-HUMAN ANIMALS

(75) Inventors: P. Alexander Derchak, Summit, NJ (US); Kathryn Lynn Ostertag, Orange, MA (US); Lance Jonathan Myers, Ventura, CA (US)

(73) Assignee: Adidas AG (DE)

( * ) Notice: Subject to any disclaimer, the term of this patent is extended or adjusted under 35 U.S.C. 154(b) by 138 days.

(21) Appl. No.: 11/932,866

(22) Filed: Oct. 31, 2007

(65) Prior Publication Data
US 2008/0255468 A1  Oct. 16, 2008

Related U.S. Application Data

(63) Continuation-in-part of application No. 11/407,034, filed on Apr. 20, 2006, which is a continuation-in-part of application No. PCT/US06/14737, filed on Apr. 19, 2006.

(60) Provisional application No. 60/673,331, filed on Apr. 20, 2005.

(51) Int. Cl.
*A61B 5/00* (2006.01)
*A61B 5/08* (2006.01)

(52) U.S. Cl. .................. 600/300; 600/301; 600/529; 600/538

(58) Field of Classification Search .............. None
See application file for complete search history.

(56) References Cited

U.S. PATENT DOCUMENTS

| | | | |
|---|---|---|---|
| 4,016,868 A | 4/1977 | Allison | |
| 4,308,872 A | 1/1982 | Watson et al. | |
| 4,373,534 A | 2/1983 | Watson | |
| 4,433,693 A | 2/1984 | Hochstein | |
| 4,452,252 A | 6/1984 | Sackner | |
| 4,456,015 A * | 6/1984 | Sackner | 600/534 |
| 4,648,407 A | 3/1987 | Sackner | |
| 4,753,088 A | 6/1988 | Harrison et al. | |
| 4,777,962 A | 10/1988 | Watson et al. | |
| 4,800,495 A | 1/1989 | Smith | |
| 4,807,640 A | 2/1989 | Watson et al. | |
| 4,815,473 A | 3/1989 | Watson et al. | |

(Continued)

FOREIGN PATENT DOCUMENTS

WO  WO2005115242  12/2005

OTHER PUBLICATIONS

Fahrenberg, "Origins and Developments of Ambulatory Monitoring and Assessment", in Fahrenberg et al., 2001, Progress in Ambulatory Assessment. Seattle, WA: Hogrefe and Huber.

*Primary Examiner*—Henry M Johnson, III
*Assistant Examiner*—Shirley Jian
(74) *Attorney, Agent, or Firm*—Sterne Kessler Goldstein & Fox PLLC

(57) ABSTRACT

This invention provides monitoring garments for non-invasively monitoring physiological parameters in un-restrained and/or restrained animals, such as monkeys, rabbits, dogs, horses, and the like. The invention also includes methods and systems for collecting and processing monitoring data and methods for recognizing apneas and other respiratory events, periods of restfulness and wakefulness, stereotypical behavior and other indicators of dysphoric states, periods of emesis, and occurrence of barking and coughing.

7 Claims, 23 Drawing Sheets

U.S. PATENT DOCUMENTS

| | | |
|---|---|---|
| 4,817,625 A | 4/1989 | Miles |
| 4,834,109 A | 5/1989 | Watson |
| 4,860,766 A | 8/1989 | Sackner |
| 4,960,118 A | 10/1990 | Pennock |
| 4,966,155 A | 10/1990 | Jackson |
| 4,986,277 A | 1/1991 | Sackner |
| 5,007,427 A | 4/1991 | Suzuki et al. |
| 5,040,540 A | 8/1991 | Sackner |
| 5,074,129 A | 12/1991 | Matthew |
| 5,131,399 A | 7/1992 | Sciarra |
| 5,159,935 A | 11/1992 | Sackner et al. |
| 5,178,151 A | 1/1993 | Sackner |
| 5,301,678 A | 4/1994 | Wilson et al. |
| 5,331,968 A | 7/1994 | Williams et al. |
| 5,348,008 A | 9/1994 | Bornn et al. |
| 5,353,793 A | 10/1994 | Bornn et al. |
| 5,416,961 A | 5/1995 | Vinay |
| 5,447,164 A | 9/1995 | Shaya et al. |
| RE35,122 E | 12/1995 | Coreman et al. |
| 5,533,511 A | 7/1996 | Kaspari et al. |
| 5,544,661 A | 8/1996 | Davies et al. |
| 5,564,429 A | 10/1996 | Bornn et al. |
| 5,588,425 A | 12/1996 | Sackner et al. |
| 5,820,567 A | 10/1998 | Mackie |
| 5,899,855 A | 5/1999 | Brown |
| 5,913,830 A | 6/1999 | Miles |
| 5,991,922 A | 11/1999 | Banks |
| 6,015,388 A | 1/2000 | Sackner et al. |
| 6,047,203 A | 4/2000 | Sackner et al. |
| 6,066,093 A | 5/2000 | Kelly et al. |
| 6,067,462 A | 5/2000 | Diab et al. |
| 6,142,953 A | 11/2000 | Burton et al. |
| 6,223,072 B1 | 4/2001 | Mika et al. |
| 6,254,551 B1 | 7/2001 | Varis |
| 6,341,504 B1 | 1/2002 | Istook |
| 6,413,225 B1 | 7/2002 | Sackner et al. |
| 6,449,504 B1 | 9/2002 | Conley et al. |
| 6,551,252 B2 | 4/2003 | Sackner et al. |
| 6,604,115 B1 | 8/2003 | Gary et al. |
| 6,633,772 B2 | 10/2003 | Ford et al. |
| 6,721,594 B2 | 4/2004 | Conley et al. |
| 6,727,197 B1 | 4/2004 | Wilson et al. |
| 6,783,498 B2 | 8/2004 | Sackner et al. |
| 7,077,810 B2 * | 7/2006 | Lange et al. ............... 600/538 |
| 2002/0090667 A1 * | 7/2002 | Ratcliffe et al. ............... 435/34 |
| 2003/0135127 A1 | 7/2003 | Sackner et al. |
| 2005/0054941 A1 | 3/2005 | Ting et al. |
| 2005/0119586 A1 | 6/2005 | Coyle et al. |
| 2005/0228234 A1 | 10/2005 | Yang |
| 2005/0240087 A1 | 10/2005 | Keenan et al. |
| 2006/0000420 A1 | 1/2006 | Davies |
| 2006/0036183 A1 | 2/2006 | Sackner et al. |
| 2006/0074334 A1 * | 4/2006 | Coyle ............... 600/529 |

* cited by examiner

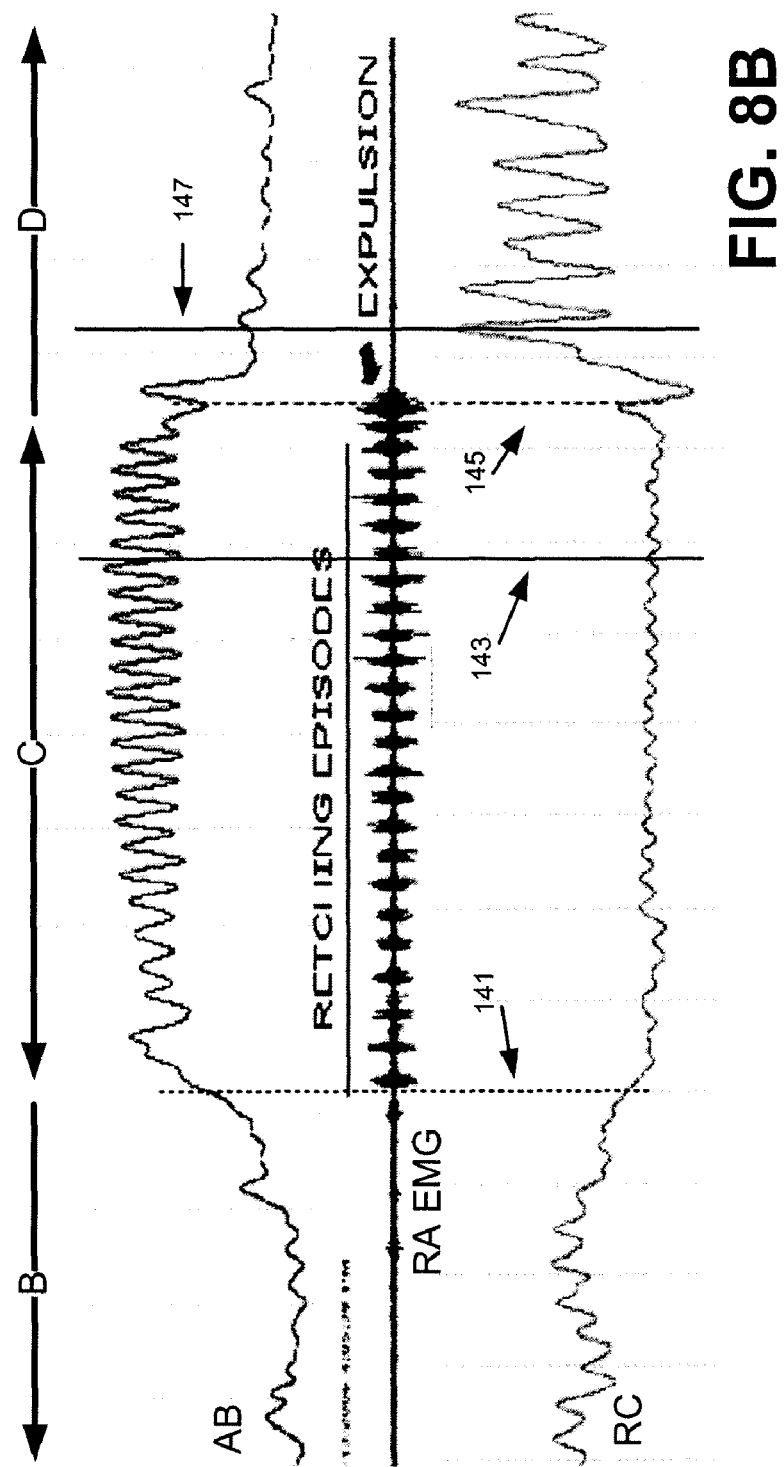

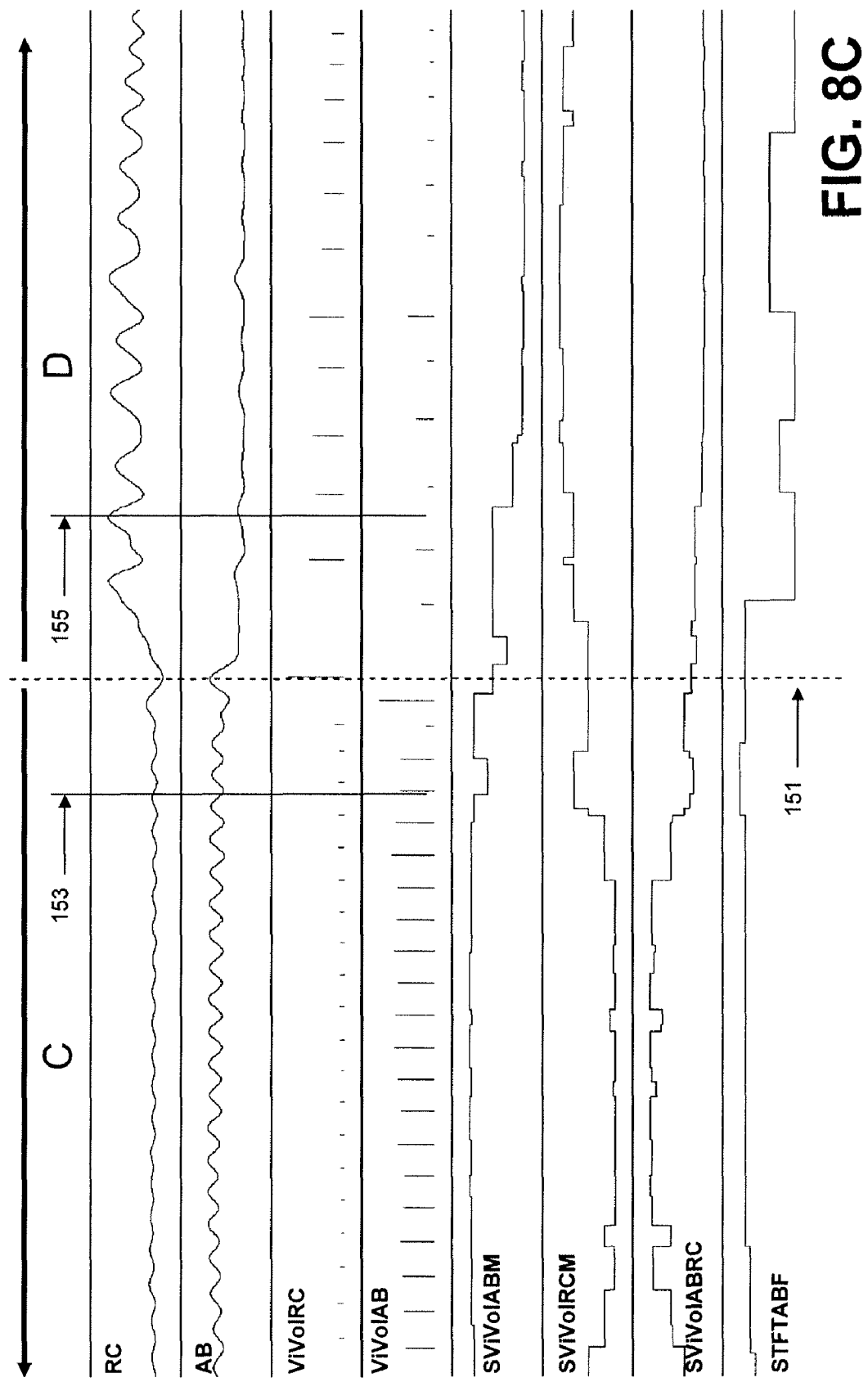

US 7,762,953 B2

SYSTEMS AND METHODS FOR NON-INVASIVE PHYSIOLOGICAL MONITORING OF NON-HUMAN ANIMALS

CROSS REFERENCE TO RELATED APPLICATIONS

This application is a continuation-in-part of prior application Ser. No. 11/407,034 filed Apr. 20, 2006, which is a continuation in part of PCT application PCT/US06/14737 filed on Apr. 19, 2006, which claims benefit of U.S. provisional application Ser. No. 60/673,331, filed Apr. 20, 2005. All three applications are incorporated herein by reference in their entireties for all purposes.

FIELD OF THE INVENTION

The present invention relates to non-invasive physiological monitoring of restrained and/or unrestrained non-human animals, and more particularly provides monitoring systems for collecting physiological data from animals and methods for collecting and interpreting data.

BACKGROUND OF THE INVENTION

Pharmaceutical compounds are subject to extensive testing before approval for general use. Early stages of this testing (pre-clinical) require demonstrating that a proposed compound is safe to administer to humans. To so demonstrate, prior to any human administration, a proposed compound is administered to animals with physiological responses similar to humans. During such animal testing, physiological and biological systems of a test animal must be monitored to detect any adverse effects that might occur. It is preferred that physiological monitoring not entail invasive procedures and that during monitoring test animals are unrestrained.

Specifically, because of their similarity to humans, primates, especially monkeys, are preferred pre-clinical testing animals. However, accurately monitoring respiratory volumes of monkeys has required physically immobilizing the monkeys and placing a face mask over their faces. Monitoring unrestrained monkeys has been possible, but only by surgically implanting into the monkey a monitoring device sensitive to intra-pleural pressure. Data returned from such an implanted device is responsive to respiratory rate, but contains virtually no information on respiratory volumes. Further, the associated surgical procedure is unpleasant at best and often painful for the monkeys, adds to monitoring expense, requires healing after surgery that delays monitoring procedures, and causes an inevitable risk of infection. And once implanted, the device is susceptible to failure and in some cases self-extraction by the monkey.

Additionally, other fields can benefit from facilities for non-invasive physiological monitoring of unrestrained animals that are currently not readily available. For example, veterinary practice, both medical and surgical, would benefit from readily available physiological monitoring of unrestrained animals. Such monitoring would also enable more precise and accurate animal evaluation and training. Such monitoring can also be beneficial to ecological or behavioral studies of free ranging animals.

For these and for other reasons, the arts are in need of non-invasive physiological testing systems that provide respiratory and other physiological data from restrained and/or unrestrained monkeys and/or other test animals.

A number of references are cited herein, the entire disclosures of which are incorporated herein, in their entirety, by reference for all purposes. Further, none of these references, regardless of how characterized above, is admitted as prior to the invention of the subject matter claimed herein.

SUMMARY OF THE INVENTION

Objects of the present invention include systems for non-invasive monitoring of physiological variables of unrestrained (or restrained) non-human animals in a manner that is pain free and that cause little or no distress to the animal. A further object is accurate monitoring of physiological variables, many of which that could not heretofore be non-invasively monitored in unrestrained animals, in many diverse environments, such as in the laboratory, in limited test facilities, in the open, or even in freely ranging animals.

According to this invention, animals are monitored by providing animal garments into which are incorporated one or more physiological sensors. Various embodiments of the animal monitoring garments of this invention are preferably adapted to the physical and behavioral characteristics of individual animal species or even of individual animals. Most often the animal species to be monitored are often mammals, especially land-dwelling mammals. However, the invention can also be applied to other vertebrate species such as amphibians or reptiles, or generally, to any animal species having physiological variables that can be non-invasively monitored.

More specifically, embodiments of this invention are directed to such non-human mammalian species as: primates, e.g., monkeys, chimpanzees, orangutans, and so forth; rodents, e.g., rats, mice, guinea pigs, and so forth; to carnivores, e.g., dogs, domestic cats, wild cats, and so forth; to cattle, horses, elephants, and the like; to pigs, e.g., mini-pigs; to weasels, e.g., minks, ferrets, and the like, and to other animals. The species can be wild-type, common, purpose bred (e.g., Yucatan, Göttingen, and other mini-pigs), and the like Monitoring garments for a selected species (or a selected individual animal) are sized and configured to fit members of that species in an unobtrusive manner and most preferably without causing distress or pain. Most preferably, monitoring can be done without requiring that an animal be constrained or restrained. While wearing an appropriate monitoring garment, an animal should be able to carry out normal life activities and to have substantially normal mobility. However, if restraint is needed in a particular application, the garments preferably allow restraint using existing restraining devices and methods but without distorting monitoring data. Since continuous and/or long-term physiological monitoring is useful in many fields, it is preferably that monitoring garments are sufficiently tolerated so that they can be worn for extended periods of time, e.g., one or more hours, or one or more days, or one or more weeks.

Monitoring garments also preferably include adjustment and fixation devices to prevent, or minimize, self-removal by a monitored animal. Also, accurate operation of many sensors requires that they remain in a fixed position relative to the animal. Harnesses, halters, collars, belts and the like can improve fixation in a longitudinal direction along an animal's body. Snaps, zippers, elastic, Velcro and the like can improve fixation in a transverse by, e.g., allowing a garment to be snugly fit about an animal. Arrangement of adjustment and fixation devices preferably accommodates an animal's motions and activities without pressuring, abrading or otherwise injuring the animal's skin and/or subcutaneous tissues. However, adjustment and fixation devices should not rigidly attach to an animal or require invasive positioning procedures. Alternatively, a garment can be individually tailored for a particular animal.

Monitoring garments incorporate one or more non-invasive sensors which collect physiological data monitoring the animal. Sensors can be incorporated into garments in many ways, for example, by weaving, or knitting, or braiding into fabric from which a garment is constructed; or by being carried in, or mounted in, or attached to a finished garment. Sensors can also be glued, printed, sprayed and so forth onto inner or outer garment surfaces. Preferred sensors collect data by being in appropriate contact with the animal without requiring applicants of ointments or creams to the animals skin. Preparation is preferably limited to shaving a portion of the animal skin. Example of preferred sensors include: a fabric or flexible electrocardiogram (ECG) electrode sewn on the inner surface of a garment so as to be in electrical contact with the animal's skin without need to conductive ointments; or one or more accelerometer attached to a snugly fitting garment so as to be sensitive to an animal's posture and motion, and so forth. Less preferably, a sensor accessible from the inside of a garment can require physical positioning or adhesion stuck to an animal's skin.

Many types of sensors can be incorporated in the monitoring garments of this invention. Commonly incorporated sensors include the following. A sensor, referred to herein as a "size sensor", gathers signals responsive to indicia of subject sizes, such as lengths, circumferences, diameters, or equivalent or similar measures, of selected portions of the animal, such as the animal's torso, neck, extremities, or other body parts, or portions thereof. Inductive plethysmography described subsequently is a preferred technology suitable for size sensors. See, e.g., U.S. Pat. No. 6,783,498 issued Aug. 31, 2004, U.S. Pat. No. 5,331,968 issued Jul. 26, 1994, and U.S. Pat. No. 4,834,109 issued May 30, 1989, all of which are incorporated herein by reference in their entireties for all purposes.

Size sensors positioned at one or more levels of an animal's trunk or torso, e.g., at an abdominal level and/or at a rib cage level, provide size data that can be usefully interpreted, according a two-component breathing model calibrated for a particular animal, to determine the animal's respiratory rates and volumes, e.g., tidal volumes. A garment fitted with such sensors can provide respiratory rate and volume data that has not previously been easily and non-invasively available. Size sensors at a mid-trunk or mid-thorax level can be responsive to cardiac and/or aortic pulsations; size sensors about one or more limbs can be sensitive to venous or arterial pulsations.

Garments can also include: electrocardiogram (ECG) electrodes and other cardiac activity sensors, e.g., fabric of otherwise flexible electrodes (see, e.g., U.S. provisional patent application No. (to be determined) filed Apr. 10, 2006 and titled "PHYSIOLOGICAL SIGNAL PROCESSING DEVICES AND ASSOCIATED PROCESSING METHODS", which is incorporated herein by reference in its entirety for all purposes); sensors for posture and activity, e.g., one or more accelerometers sensitive to an animal's orientation with respect to gravity and to an animal's accelerations accompanying activity; temperature sensors, e.g., thermistors; blood oxygen levels, e.g., pulse oximeters, electrodes for cerebral electrical activity, muscle electrical activity including activity of ocular muscles; and the like.

This invention also includes electronic circuitry variously housed that cooperate in a sensor specific manner with sensors incorporated into a monitoring garment to retrieve, process and store, and optionally display physiological data from a monitored animal. In preferred embodiments, such electronic element is a single portable data unit (PDU) (in one or two housings) that is in the vicinity of a monitored animal. A PDU serves to operate sensors, to retrieve sensor data, and to process retrieved data at least so that it can be digitally temporarily stored and/or transmitted for possible use by systems external to the immediate environment of the animal. Temporary data storage can be in flash memory or on magnetic media, e.g., hard drives, and data so stored can be transmitted by removing the flash memory or hard drive. Immediate transmission can be by wired or wireless links.

In these embodiments, PDUs can be carried on and by an animal preferably and operate autonomously so that the animal need not be restrained by data, power or other types of cables between the PDU and outside systems. Such PDUs should be sized and configured not to hinder the animal's activities and not to be obtrusive or significantly apparent to the animal. Such PDUs are accordingly preferably sized and configured to fit into a pocket or a recess of the monitoring garment itself, or to be carried a pack or a backpack outside of the garment (but not accessible by the animal) or otherwise carried. Such PDUs preferably either store data, e.g., for later analysis, or wirelessly transmit data, e.g., for real-time analysis. For example, animal monitoring facility can have a central collection system in communication with multiple monitored animals with such PDUs.

Alternatively, PDUs can be connected to external systems by a wire or cable; the animal can then move freely but only within a specified area. Such PDUs do not need to function autonomously. For example, their functions can be limited to interfacing with sensors and sending retrieved sensor data to external circuitry that resides away from an animal for storage, retransmission, processing, or the like.

PDUs carried by an animal can be connected to their controlled sensors incorporated into a garment worn by the animal in various manners. In one alternative, sensors can be linked to PDUs by wires and/or cables, all of which are preferably routed in a single physical data cable. In this embodiment, the PDU function can be performed by circuitry in two or more housing all linked by cables. In another alternative, sensors can be linked to the PDU by wirelessly means using, e.g., Bluetooth or similar local transmission technologies.

This invention also includes external computer systems that can receive animal monitoring data from the PDUs, process received data, display processed data, and store raw and/or processed data. These computer systems can be variously configured according to the processing needs of an animal monitoring application, and they can range from a single PC-type computer suitable for monitoring a limited number of animals to server-type distributed systems for monitoring a larger number of animals. These systems are generally located external to the immediate animal environments and may be local or remote to the animal monitoring facility itself and perform methods carrying out the following functions. The external systems can be format and display raw and/or processed sensor data and can also archive raw and/or processed data.

Sensor data can be processed by the external systems and/or also by the PDUs. Sensor-specific processing functions can be assigned to these components according to their relative capabilities and according to processing requirements of data retrieved from various sensors. Data from some types of sensors needs can require more extensive processing. For examples, respiratory signals from size sensors are preferably calibrated and combined according to a calibrated two-compartment breathing model in order to provide respiratory volumes. Respiratory rates and further respiratory events can then be extracted from the processed respiratory volume data. Heart beat occurrences and heart rate can be extracted from raw ECG signals by applying known signal processing methods. Accelerometer data is preferably processed to determine animal posture, e.g., as reflected in accelerations of lower temporal frequencies that likely arise from an animal's orientation with respect to gravity, and to determines animal activity, e.g., as reflected in higher-temporal-frequency accelerations that likely arise from an animal's movements or activities. Data from other types of sensors needs less extensive processing, e.g., limited to filtering to limit noise and artifacts. Such data includes, for example, temperature signals, cerebral and/or muscular electrical activity, and the like.

Although this invention is usefully applied during the course of pharmaceutical testing, it will be appreciated that non-invasive monitoring of (optionally) unrestrained animals has numerous other applications. For example, this invention can usefully monitor laboratory mammals of all sizes during basic and applied research. It is useful throughout the fields of veterinary medicine and surgery, for example for continuous physiological monitoring during veterinary care of animal patients, from pet mammals to commercial mammals (e.g., cattle), and also in testing veterinary pharmaceuticals. This invention is also useful in general animal training and monitoring programs. It can be used for training racing dogs and horses. It can be used in zoos for monitoring animals in need to veterinary attention, for animal research, or for other purposes.

This invention also includes computer readable media on which the methods are encoded.

Specific embodiments of this invention will be appreciated from the following detailed descriptions and attached figures, and various of the described embodiments are recited in appended claims.

BRIEF DESCRIPTION OF THE DRAWINGS

The present invention may be understood more fully by reference to the following detailed description of preferred embodiments of the present invention, illustrative examples of specific embodiments of the invention, and the appended figures in which:

FIGS. 8A-C illustrate exemplary monitoring data obtained from a canine;

DETAILED DESCRIPTION OF THE PREFERRED EMBODIMENTS

Figure 1A:
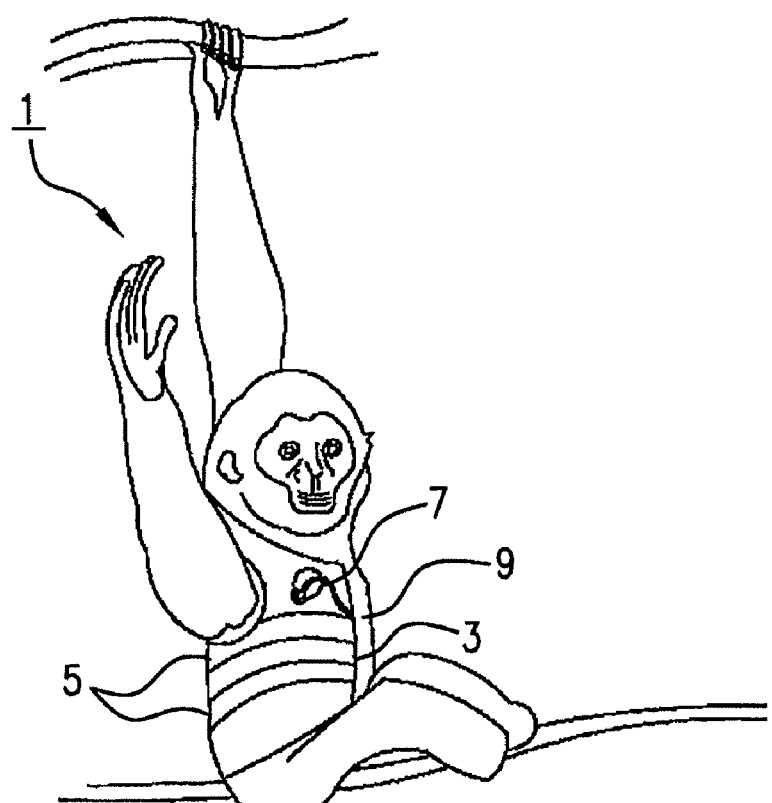
FIGS. 1A-E illustrate embodiments of animal monitoring garments.

The present section describes in more detail certain preferred but non-limiting embodiments of this invention. Headings and legends are used here, and throughout this application, for clarity only and without intended limitation.

Contrary to expectations, the inventors of this application have discovered that selected technologies known to be useful for monitoring ambulatory human subjects are also surprisingly successful for monitoring unrestrained (and/or restrained) non-human subjects. In particular, size sensors incorporated in a garment for an animal subject in a manner so that they are appropriately positioned on an animal subject wearing the garment provide useful and accurate respiratory and cardiac data. Further, the inventors have observed that selected secondary sensors, incorporated in such a garment many, return data useful for supplementing and interpreting size sensor data. These secondary sensors are also known for use in human monitoring. Accordingly, described herein are sensor technologies and preferred garment structures incorporating sensors based on the preferred technologies.

Preferred Sensor Technologies

Monitoring garments of this invention preferably include one or more size sensors, although certain embodiments of this invention include monitoring garments without any size sensors. Useful size sensors are known that are based on diverse technologies including: magnetometers; piezoelectric strain gauges; magnetic or capacitive strain gauges; electrical impedance and/or activity at the body surface; optical techniques including interferometry; pressure-based plethysmography, ultrasonic measurements; and so forth. See, e.g., U.S. Pat. No. 5,373,793 issued Oct. 11, 1994.

Preferred size sensors are based on inductive plethysmography ("IP"), and especially preferred are IP sensor configured and arranged to measure body wall size changes due to respiration (respiratory IP or "RIP"). IP and RIP technology for human monitoring is known. Here a brief summary is provided.

IP technology responds to sizes by measuring the self-inductance of a conductor or of a conductive loop (metallic or non-metallic) arranged to snugly encircling an anatomic portion to be measured. Conductive loops can be directly incorporated (as by weaving, sewing, knitting or the like) into the fabric of a monitoring garment, and the garment designed to fit snugly so that loop sizes accurately reflect the sizes of the anatomic portion being measured. Alternatively, IP sensor conductors or conductive loops can be incorporated into bands which are affixed to garment by sewing, weaving, and the like. To measure respiratory motions, a RIP sensor should be at the level of the chest or thorax. A second RIP sensor at the level of the abdomen is preferred. In general, one or more RIP sensors should be positioned on an animal so the major components of respiration-induced body wall motion is sensed. For monkeys and smaller animals, sensitivity is increased if an IP conductive filament encircles the body part to be measured two or three or more times, or alternatively, is duplicated, e.g., by coursing back and forth in a body region.

IP signals are generated by oscillator/demodulator modules linked to variable-inductance IP sensors. As inductance changes, oscillator frequency changes. The frequency changes are demodulated and digitized. The digital data encoding the variable oscillator frequency is analyzed to determined physiological events, e.g., respirations or heartbeats. Advantageously, prior to monitoring, RIP or other IP signals are calibrated during a period of relative to more accurately reflect relative or absolute lung volumes. The oscillator/demodulator circuitry is preferably located near to the RIP sensor, e.g., in a PDU carried by the animal.

IP and RIP technologies are described in the following U.S. patents and applications. The inventors have discovered that selected portions of this technology is useful for monitoring non-human animals. See, e.g., U.S. Pat. Nos. 6,551,252 issued Apr. 22, 2003; 6,047,203 issued Apr. 4, 2000; 6,341, 504 issued Jan. 29, 2002; 5,331,968 issued Jul. 26, 1994; 5,301,678 issued Apr. 12, 1994; and U.S. Pat. No. 4,807,640 issued Feb. 28, 1989. Also see, e.g., U.S. U.S. patent application Ser. Nos. 10/822,260; and 11/233,317 filed Sep. 21, 2005. These U.S. patents and applications, and other references throughout this application, are incorporated herein in their entireties for all purposes.

ECG electrodes preferably are flexible and require little if any conductive pastes and the like in order to establish electrical contact with a monitored subject. Such electrodes can be constructed from known conductive fabrics. See, e.g., U.S. patent application Ser. No. 60/730,890 filed Oct. 26, 2005. Accelerometer sensors are preferably miniaturized MEMS-type devices sensitive to three components of acceleration Preferred Monitoring Garment Structures Monitoring garments described here in more detail are directed to monitoring monkeys, dogs, and horses. However, this invention can readily be adapted a wide range mammalian species including, e.g., mice, rats, rabbits, ferrets, guinea pigs, special bred pigs (including species of Yucatan and Göttingen mini pigs), common swine, cats, primates, sheep, cows and other cattle, and the like. Adaptation involves tailoring a garment to species sizes, providing attachment and fitting devices that hold the garment snugly and prevent self-removal, and calibrating sensor data to reflect species physiology. Attachment and fitting devices can adapt structures known in the art, e.g., harnesses, collars, halters, and the like. For small animals, more sensitive sensors are advantageous (as has been described for IP sensors). Land-dwelling vertebrates and non-mammalian species generally can be monitored if the species members are capable of wearing a monitoring garment, and particularly if they produce body wall motions indicative of useful physiological parameters.

In more detail, the monitoring garment and/or PDU and/or PDU carrier are adapted to the characteristics and behavior of the animal species to which they are directed. Garment configurations, e.g., shirt-like, or vest-like, or band-like, or the like, should be acceptable to the animal. For example, they should not obstruct the animal activities, nor unnecessarily limit the animals seeing, or hearing, or smelling, and other senses that might be vital to the species, nor cause body temperature abnormalities, and the like. Different animals scratch, claw, chew, pull, rub, and tear (especially monkeys), bite and the like, and the garment and PDU carrier should be resistant to the animal's natural abilities. Animals also run, jump, swing, hit objects, play, and the like, often quite roughly, and the garment and PDU carrier should be sufficiently mechanically strong and shock resistant so not to be damaged and even to continue operating during the animal's natural activities. The monitoring garment should also permit animal restraint by standard methods or procedures should such restraint be otherwise necessary.

Additional protection is preferable for garments that have externally accessible features, e.g., adjustments, zippers, flaps, pockets, electrical leads, and the like, and for garments worn by species that are sufficiently dexterous to be able to access and manipulate a garment, e.g., primates. External features are more susceptible to being deranged during the normal activities of any animal. They may also be accessible to the animal and damaged by pulling, chewing, biting, and so forth. One preferred form of further protection is an over-garment covering all of part of the monitoring garment and having a substantially uniform texture and without any externally accessible features. An over-garment preferably smoothes external spatial structures of the monitoring garment, such as bumps, ridges, recesses and so forth, so that they are less, or not at all, externally apparent to the animal's visual and/or tactile senses. The over-garment should by sufficiently tough not to be penetrated by the animal.

Embodiments of monitoring garments for a variety of animals are now described with reference to FIGS. 1A-E. FIG. 1A illustrates a vest-like garment 3 for un-restrained monkey 1. This garment incorporates two ECG electrodes 7 (only one is visible) in contact with the monkey's skin. In a more preferred embodiment, the illustrated cutout is absent, and ECG electrodes are mounted directly on the inside of the garment. This garment also incorporates two size sensor bands 5 returning data reflective of the sizes of the monkey's abdomen and rib cage that are useful for determining respiratory rates and volumes using a two-compartment breathing model. Longitudinal fasteners 9 such zippers and/or Velcro strips join the garment along the ventral midline.

Figure 1B:

FIG. 1B illustrates a different view of a more preferred vest-like monitoring garment 4 for monkey 10 lacking cutouts for ECG electrodes. Instead, ECG electrodes are positioned inside the garments in contact with the monkey. Longitudinal fasteners 9 along the garment's ventral midline are more clearly apparent herein.

Not illustrated but preferred, is an over-garment protecting the monitoring garment itself from the monkey. Monkeys are intelligent, dexterous and clever animals that have particular tactile sensitivity to small shapes and textures. Therefore, the over-garment preferably presents a uniform texture to the monkey's tactile senses and makes less prominent any spatial structures in the underlying garment, such as may be presented by bands, electrical leads, adjustments, fastenings, and so forth. Further, the monitoring garment, the accompanying PDU and/or PDU case or housing, and an optional over-garment should be sufficiently tough and resistant so that a monkey's often rough and sudden activities will not damage the monitoring components.

Figure 1C:
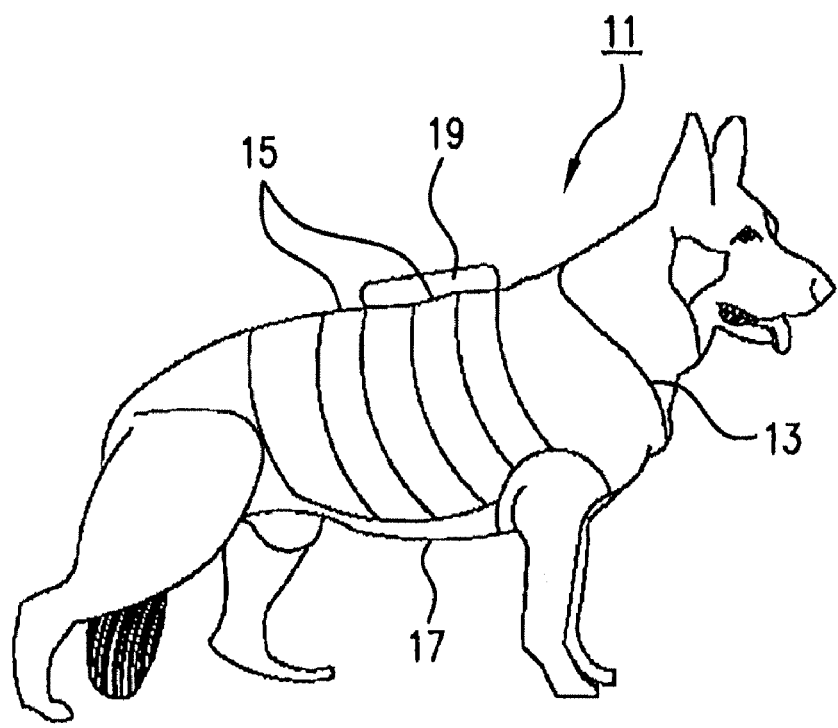

FIG. 1C illustrates a more shirt-like monitoring garment 13 for un-restrained dog 11. This garment extends relatively further in the longitudinal direction along the dog's torso than does the more vest-like garment of FIG. 1A. This provides longitudinal stability and fixation during the dog's normal activities. This garment also includes two size sensor bands 15 suitable for obtaining data for respiratory rates and volumes. The garment is fastened by fastener 17 along the ventral midline. ECG electrodes are mounted under the garment in contact with the dog and not externally visible in garment cutouts. An over-garment (also not illustrated) is also preferred for dog monitoring The garment of FIG. 1C includes backpack 19 which carries the PDU safely on the dog's back out of the dog's reach. A data cable not illustrated and not accessible by the dog links the PDU to the garment sensors. It can be routed along and under an upper seam of the garment to the ventral midline along which it connects to sensors and to sensor electronic modules.

Figure 1D:
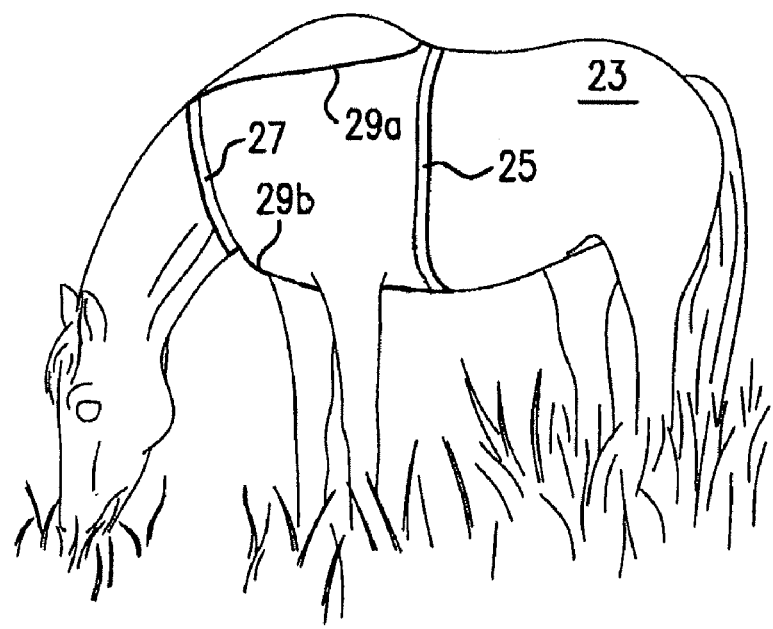
Figure 1E:
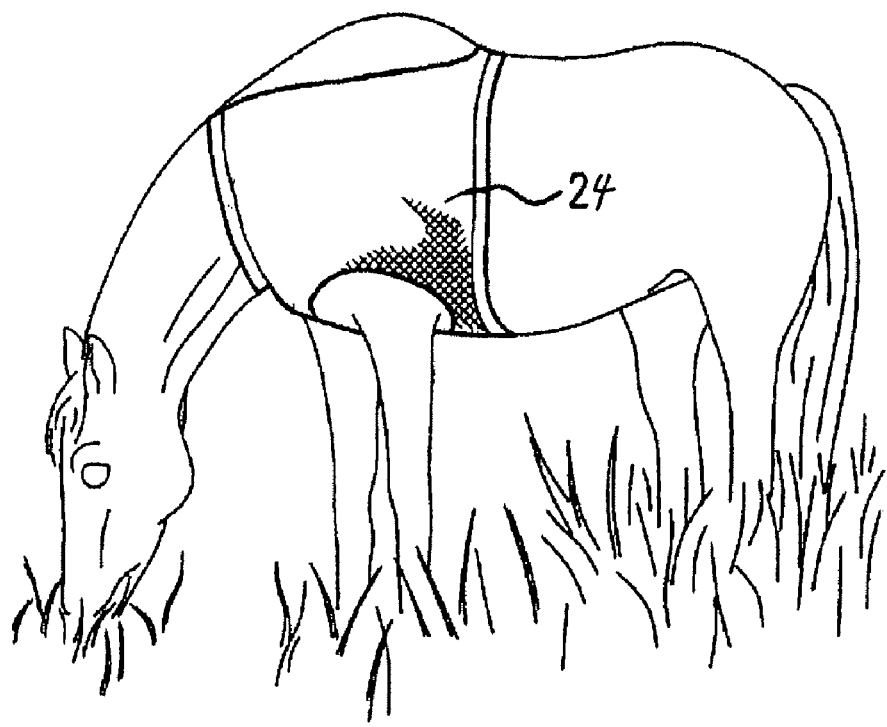

FIG. 1D illustrates a band-like garment for un-restrained horse 23. This garment includes band 25 incorporating one or more size sensors for monitoring the horse's respiratory rate and optionally respiratory volumes. The band may also incorporates ECG electrodes in contact with the horse ventrally. This band-like garment can be secured and fixed on the horse in a variety of ways. Illustrated is harness arrangement 27 connecting to the monitoring garment with dorsal strap 29a and ventral strap 29b and anchoring the garment with respect to the horses neck. Alternatively, band 25 may be displaced to an abdominal position and the garment may include a second band in the vicinity of the horses front legs. Thereby, the band is relatively fixed so that both rib cage and abdominal sizes may be obtained for more accurate respiratory volumes. In another embodiment shown in FIG. 1E, the monitoring garment 24 has a vest-like configuration similar to the garment of FIG. 1C, except that the garment 24 is adapted to fit, preferably snugly, to the physiological characteristics of a horse.

Alternatively, a horse can be provided with a vest-like or shirt-like monitoring garment incorporating sensors. A preferred such shirt-like garment has a relative configuration and size similar to garment 13 illustrated for dog 11 (FIG. 1C) but of an appropriately larger scale.

Figure 2A:
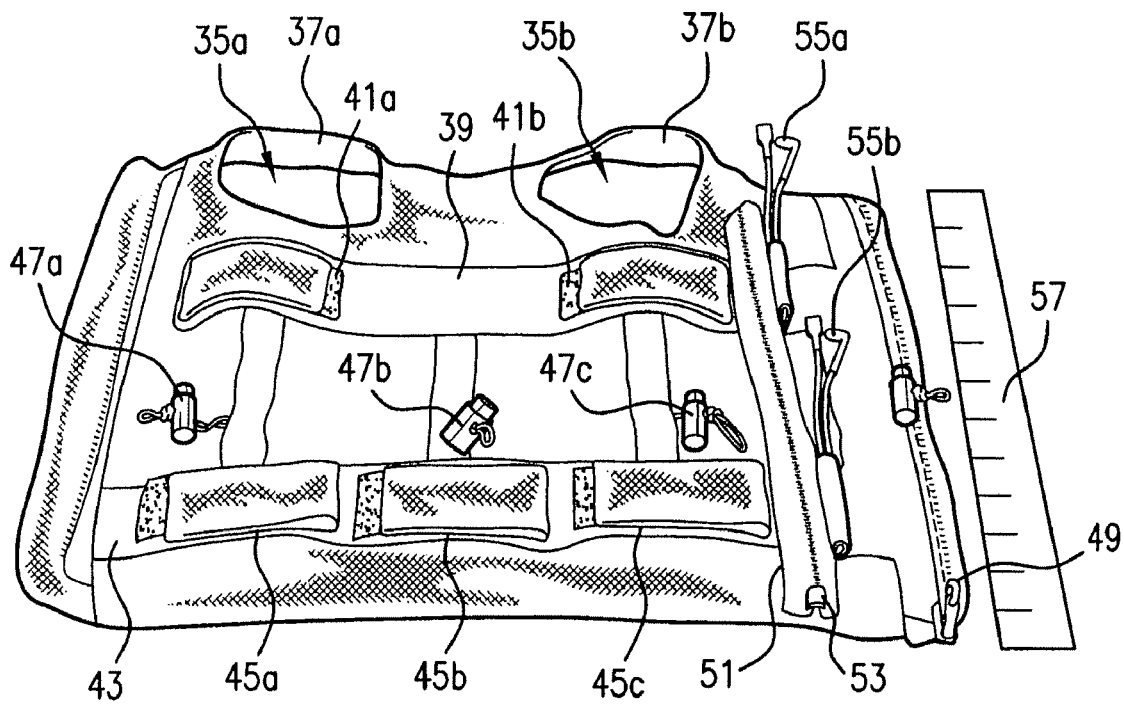
FIGS. 2A-E illustrate views of an exemplary monitoring garment for a monkey.

FIGS. 2A-E illustrate several views of an actual monitoring garment for a small primate, particularly a monkey. Twelve inch ruler (57 in FIG. 2A) provides a scale for the garment. FIG. 2A is a view of the outside of an extended garment. Rostrally are arm holes 35a and 35b with shoulder straps 37a and 37b. Moving caudally, first size sensor band 39 carries Velcro adjustments 41a and 41b. By adjusting these straps, size sensor band 39 can by snugly configured about monkeys of differing sizes. Second size sensor band 43 carries three Velcro adjustments 45a, 45b, and 45c by which this second band can also be snugly configured about a monitored monkey. The garment is substantially fixed longitudinally and transversely on the monkey by cooperation of snug size sensor bands and the shoulder straps. Thereby, sensors can be relatively fixed and repeatedly placed with respect to the monkey's body so that data is accurate and consistently interpretable. Running longitudinally between the two straps are longitudinal adjustments 47a, 47b, and 47c having drawstrings with spring clips for configuring the garment so that the size sensor bands do not move relative to each other in a longitudinal direction during the monkey's normal activities. Other embodiments employ other combinations of these and other adjustment devices suitable for snugly configuring garments and achieving accurate fixation of sensors relative to the monkey.

A garment is fastened onto a monkey by first closing zipper fastener 49 that links the left and right edges of the garment. Next, right flap 51 is fastened to a corresponding left flap by zipper fastener 53. These flaps form a protected longitudinal tunnel-like arrangement which can hold electronic modules that are advantageously located close to their respective sensors. In the case of IP size sensors, electrical leads 55a and 55b emerging from under longitudinal flap 51 connect to oscillator/demodulator electronic modules placed in this tunnel. A data cable runs longitudinally along the tunnel linking these electronic modules and other sensors to the PDU carried outside the garment. Alternatively, the data cable will link to a PDU pocket if the PDU is sized so that it can be carried in a pocket of the garment.

Figure 2B:
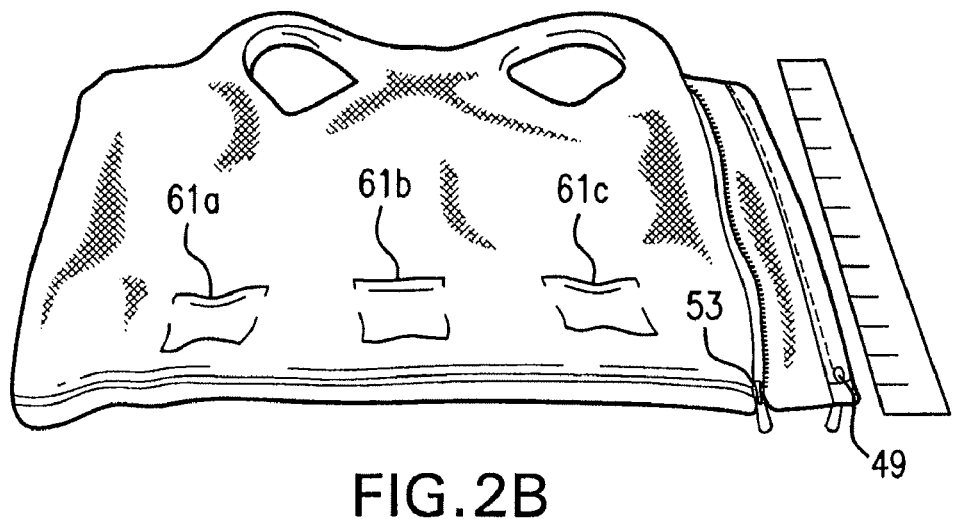
Figure 2C:
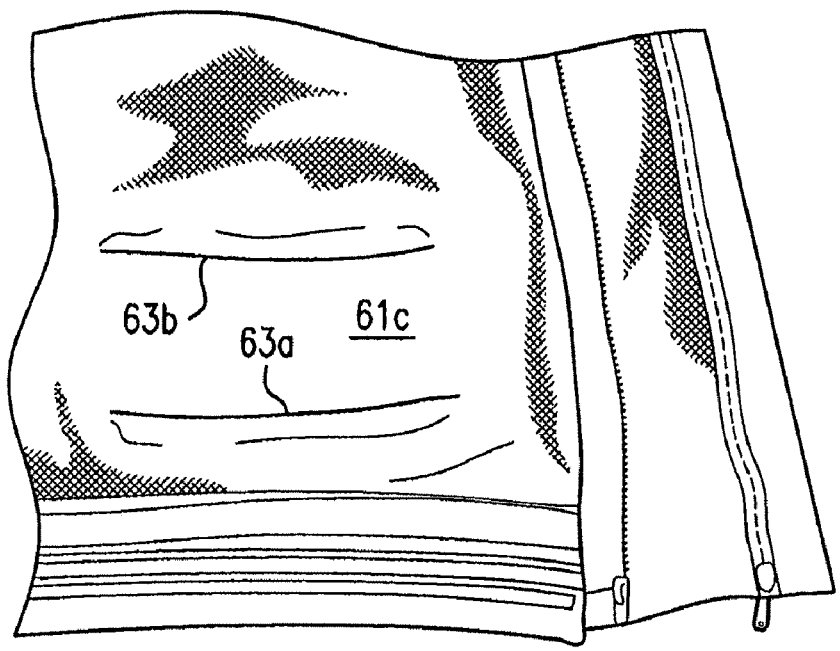

FIG. 2B is a view of the inside of an extended garment. Arm holes 35a and 35b, shoulder straps 37a and 37b, and fasteners 49 and 53 are visible. Pocket-like arrangements 61a, 61b and 61c are for holding sensors not directly woven, knitted, stitched, or otherwise directly incorporated into the garment. FIG. 2C is a detail view of the inside of sensor pocket 61c illustrating access openings 63a and 63b.

Figure 2D:
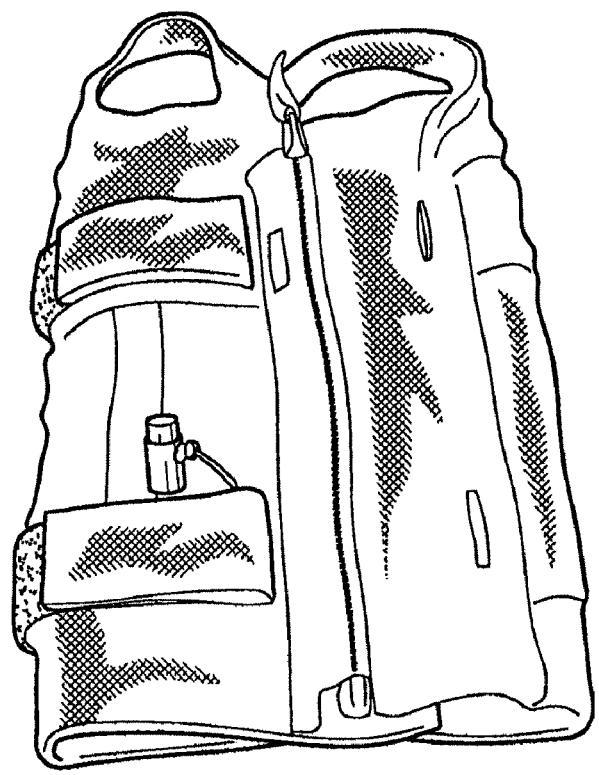
Figure 2E:
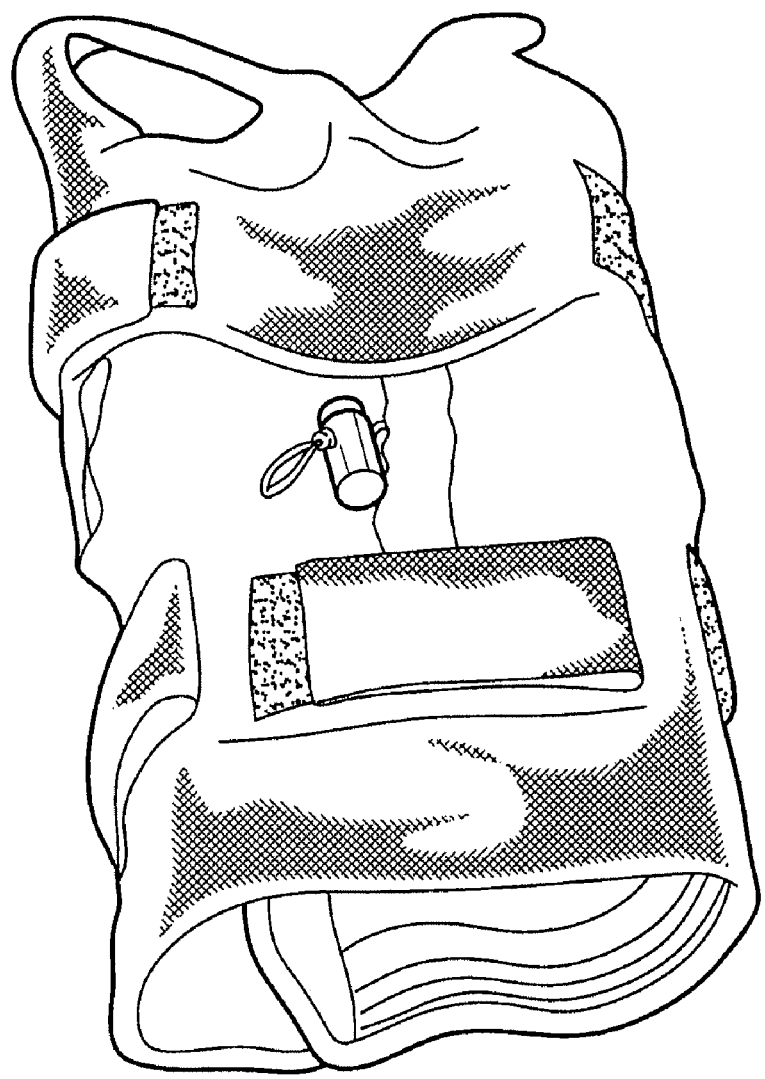

FIG. 2D is a right lateral view of a fastened garment as it would be worn by a monkey illustrating how the garment encloses the animal's torso. FIG. 2E is a similar left lateral view of a fastened garment.

Sensor processing methods are preferably specifically calibrated for monitoring specific animals and programmed in a convenient computer language, such as assembly language, C, or C++. This code can be compiled into executable form and stored on a computer readable medium for loading into a processing system of this invention. In alternative embodiments, the methods are implemented in firmware, e.g., an FPGA, and configuration instructions can be similarly stored on a computer readable medium. Accordingly, the present invention also includes program products including such computer readable media, and systems for processing the methods which receive data from the monitoring garments of this invention

EXAMPLES OF THE INVENTION

Example 1

Figure 3A:
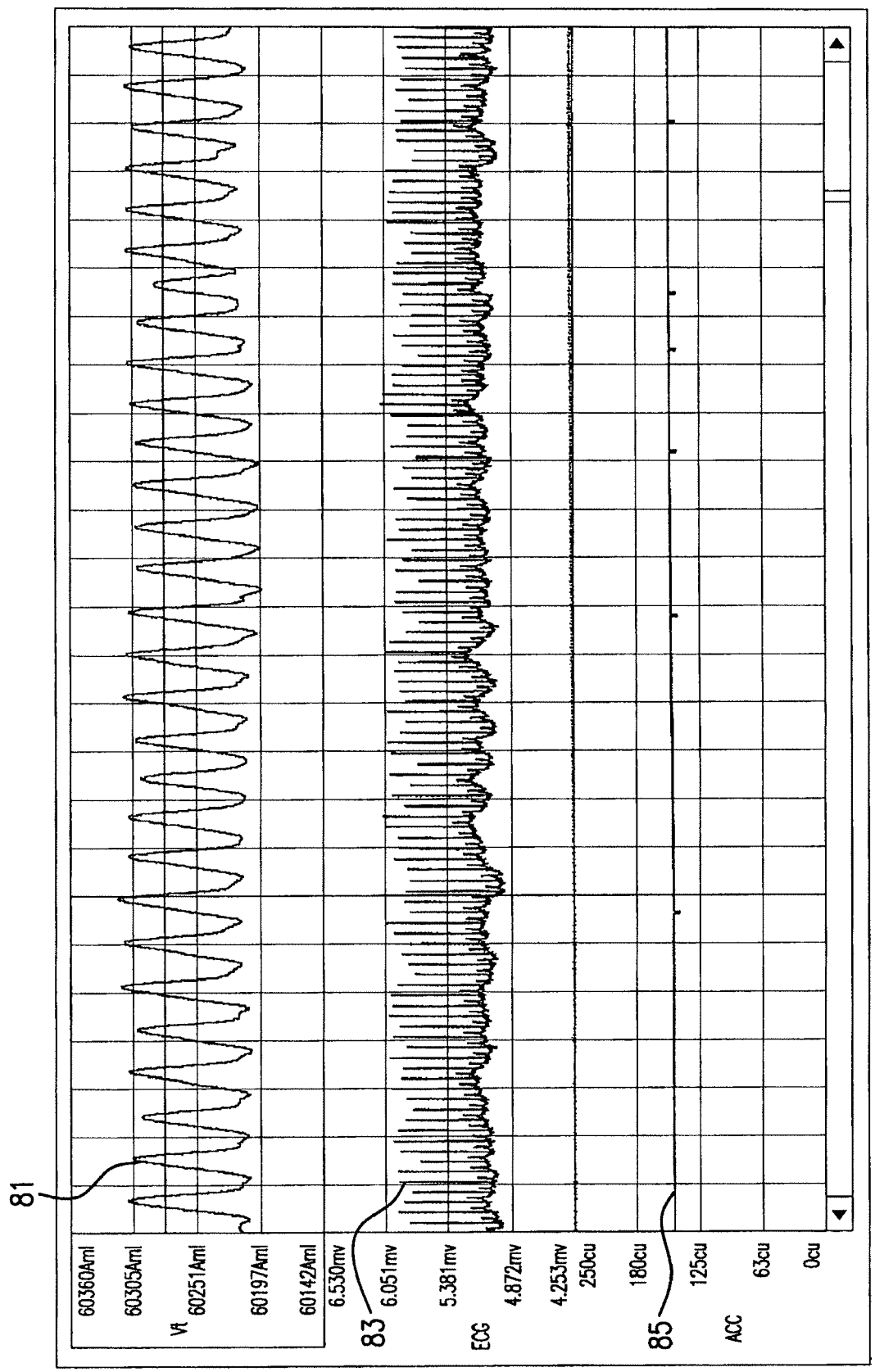
FIGS. 3A-B illustrate exemplary monitoring data obtained from a monkey.
Figure 3B:
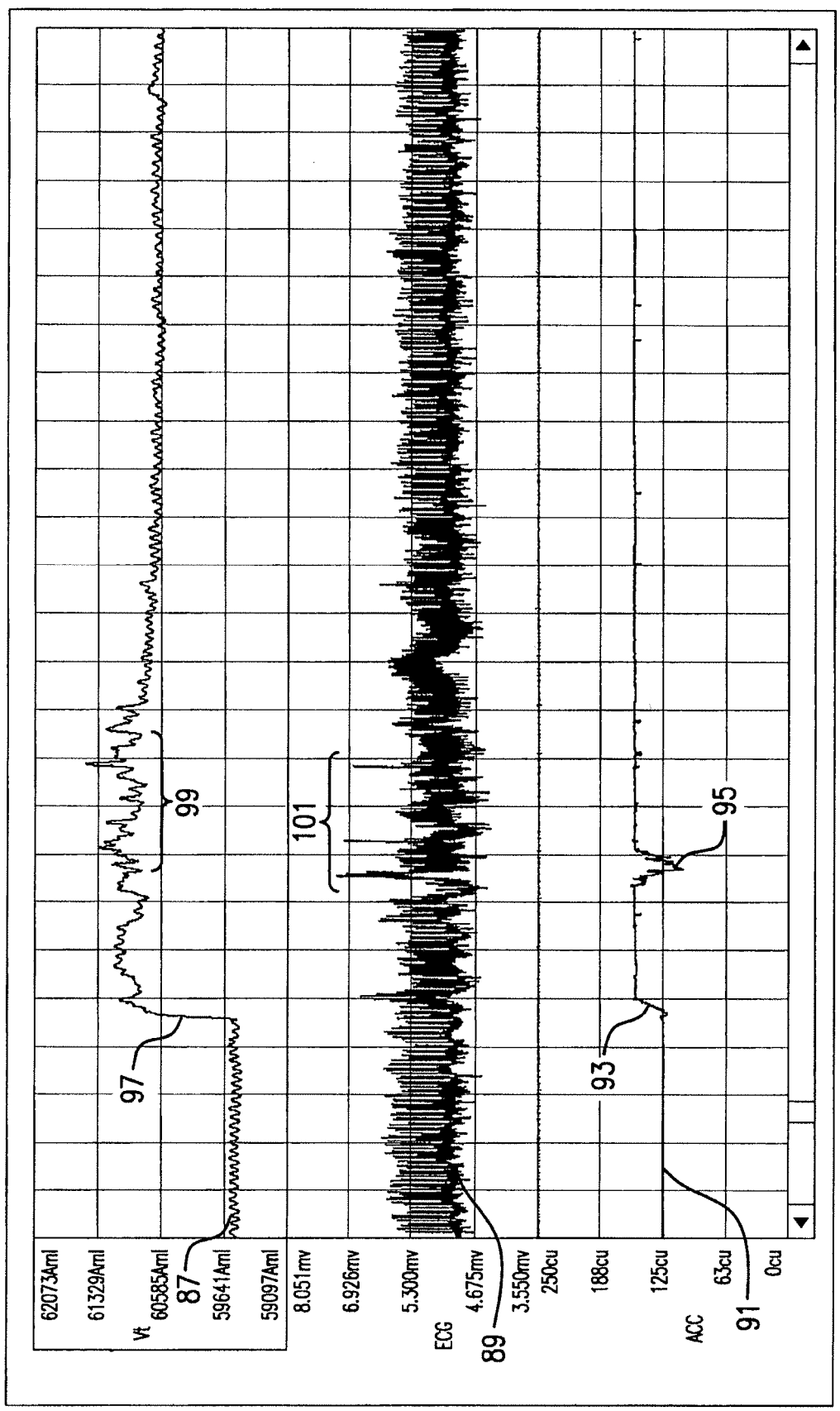
Figure 3C:
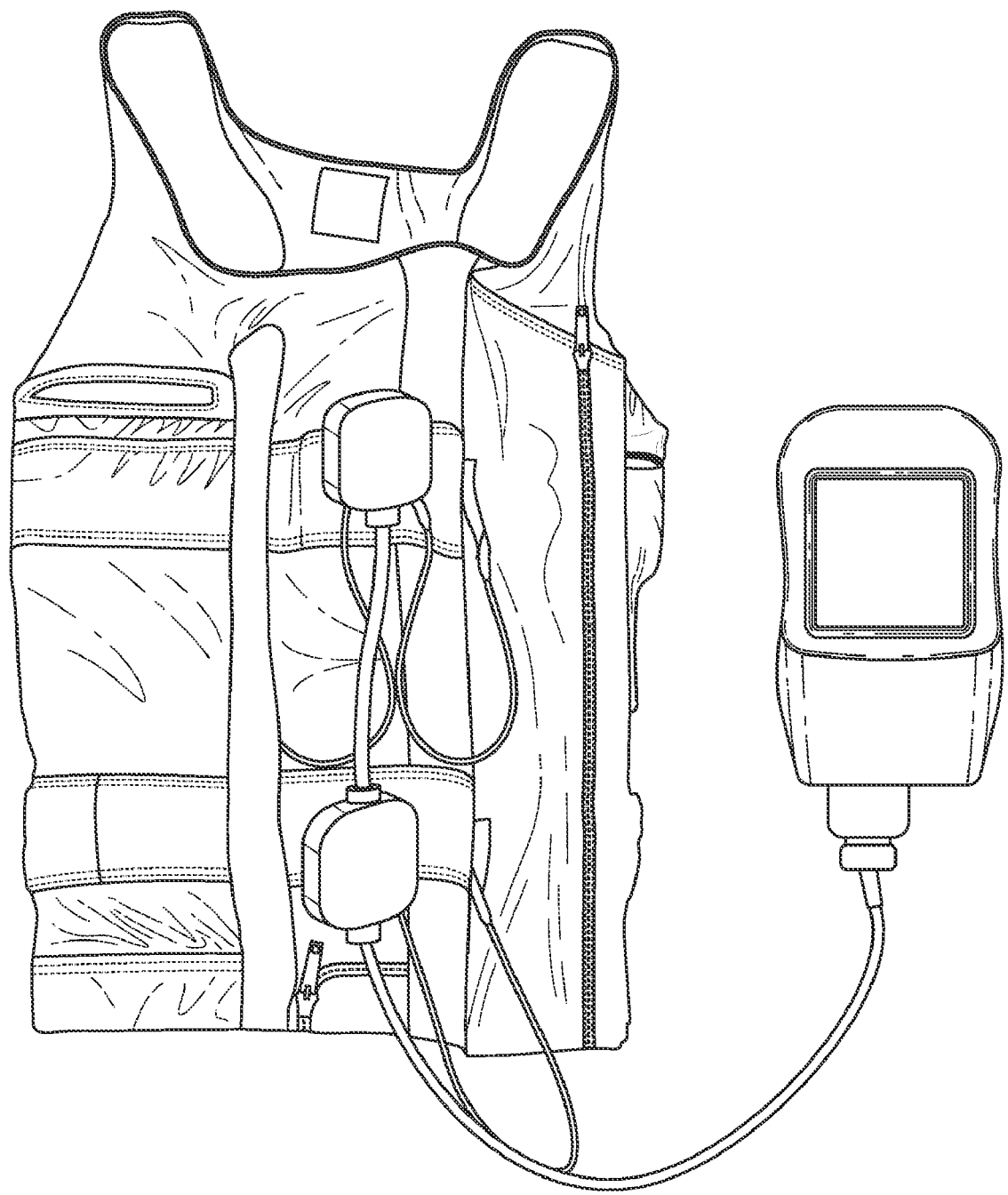
FIG. 3C illustrates an embodiment of a monitoring garment for a monkey.

FIGS. 3A and 3B illustrate processing of monitoring data from a monkey obtained with the monitoring garment of FIG. 3C, which has substantially similar features to the monitoring garment embodiment of FIGS. 2A-E. The monitoring garment of FIG. 3C also incorporates the electrical circuitry and configurations that are described in more detail in U.S. Pat. No. 6,551,252, which is expressly incorporated herein for all purposes in its entirety thereto.

FIG. 3A illustrates one minute of processed respiratory and accelerometer data along with an ECG signal also obtained using the monitoring garment. Band 85 illustrates processed accelerometer data, and shows that during this minute of data the monkey engaged in little activity and made no posture changes. Band 81 illustrates the monkey's tidal volume during this period of substantially little activity, and shows that the monkey was breathing at a regular rate with regular tidal volumes. Band 83 illustrates ECG data and shows a regular heart beat and little or no signal artifact.

FIG. 3B illustrates three minutes of data. The processed accelerometer data, band 91, indicates that at time 93 that the monkey made a change of posture and that at time 95 the monkey was briefly active. Band 89 illustrates the ECG data obtained, and band 87 illustrates the monkeys tidal volume, but a vertical scale much reduced from that of FIG. 3A. Aspects of the data displayed in bands 87 and 89 can be interpreted in view of processed accelerometer data in band 91. For example, respiratory data in band 87 illustrates that the DC volume calibration of the monkey's respiratory volume curve changed 97 along with the monkey's change of posture. Such calibration changes commonly follow posture changes, because posture significantly affects mechanical relationships in the chest and the chest's orientation with respect to gravitational acceleration. Also, both the respiratory band and the ECG band illustrate a brief period of motion artifact, 99 and 101, respectively, in association with the monkey's motion revealed at 95 in the accelerometer trace.

Example 2

Figure 4A:
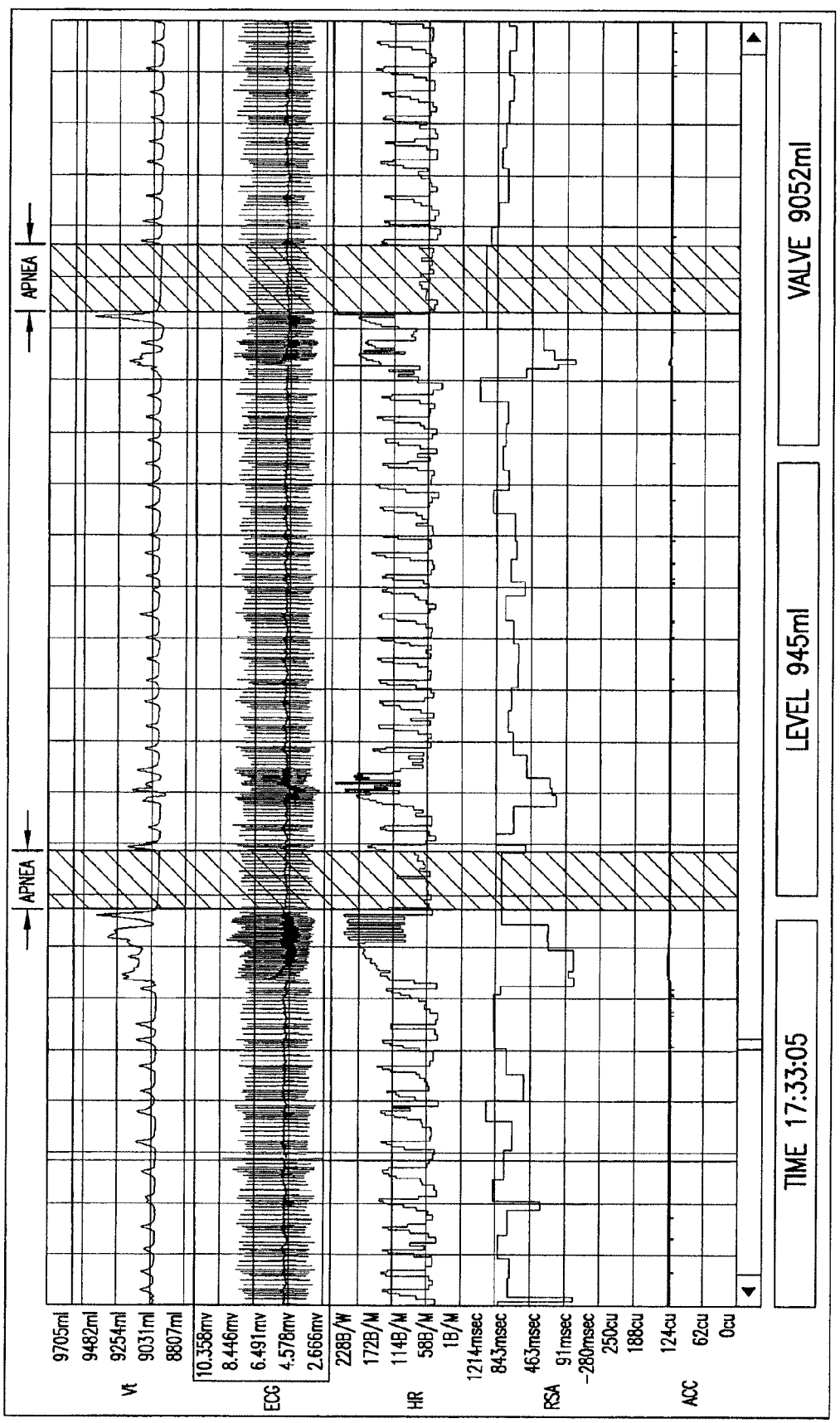
FIGS. 4A-B illustrate exemplary monitoring data obtained from a beagle.
Figure 4B:
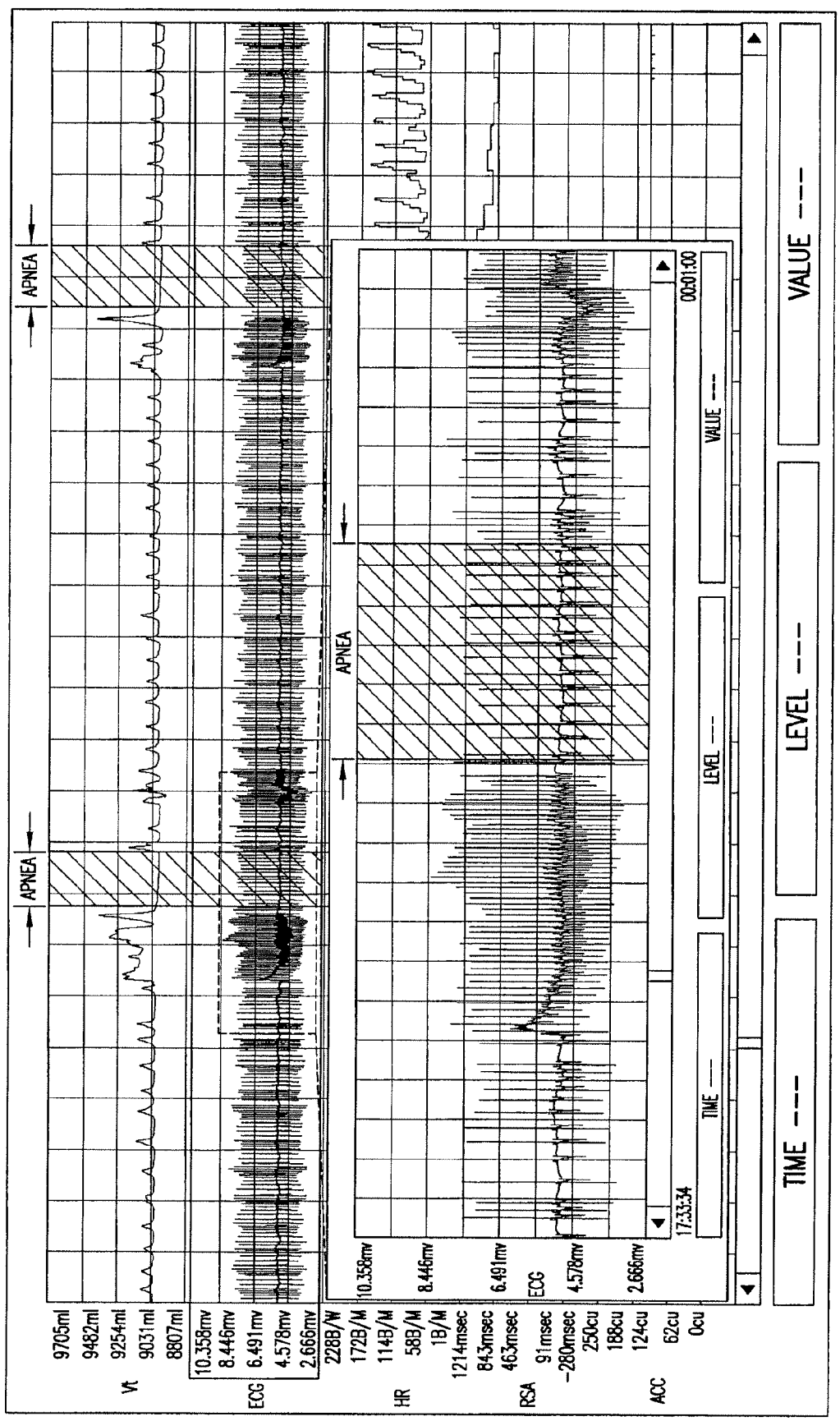
Figure 4C:
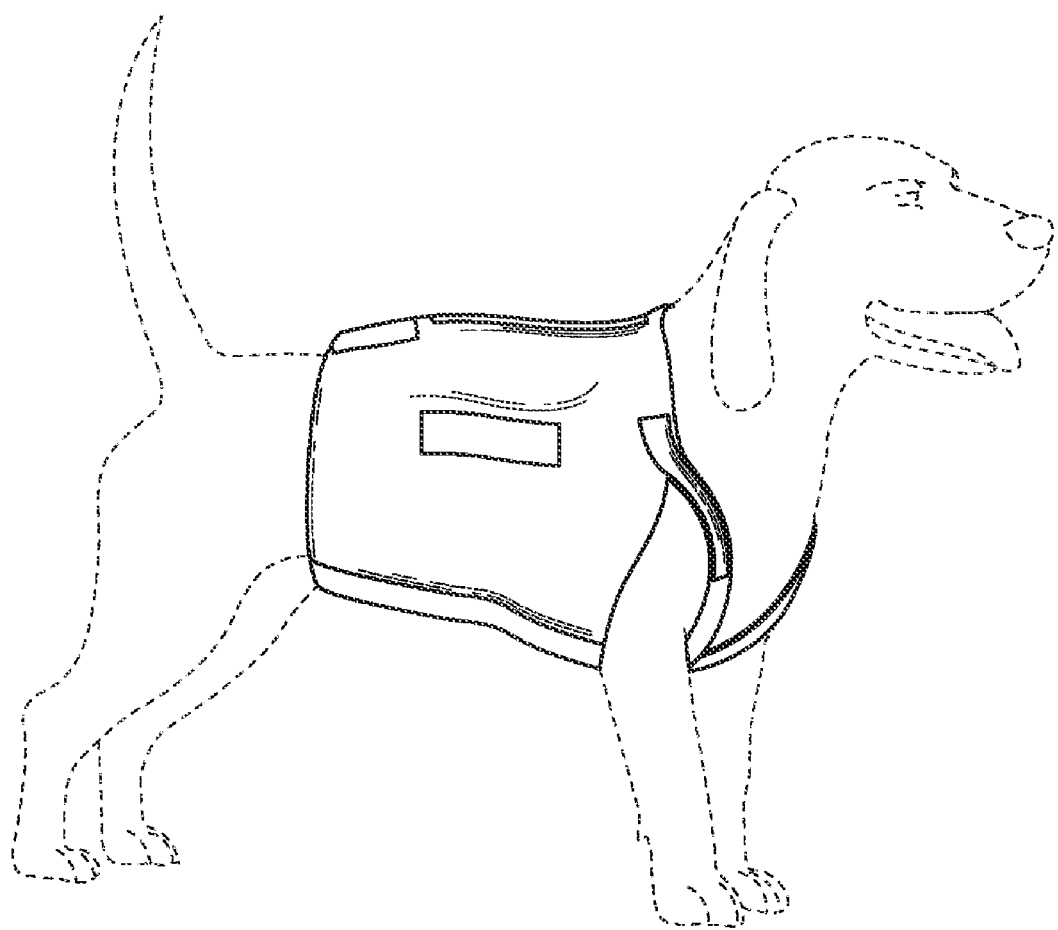
FIG. 4C illustrates an embodiment of a monitoring garment for a dog.

FIGS. 4A and 4B illustrate processing of monitoring data from a beagle obtained with a monitoring garment of FIG. 4C, which has substantially similar features to the monitoring garment adapted to fit a monkey shown in FIG. 3C. FIG. 4A illustrates five minutes of processed data including tidal volume ($V_t$), ECG, heart rate (HR), and accelerometer (ACC)

data, and an index of respiratory sinus arrhythmia (RSA). By measuring the combination of respiratory and ECG signals in an unrestrained animal, clear identification and evaluation of periods of 'pure' ECG, i.e., those unaffected by the respiratory cycle, can be made. Utilization of these stable periods for the analysis of the timing components of the ECG signal (e.g., Q-T interval) provides investigators an opportunity for greater precision thereof than is currently possible.

Specifically, during periods of central apnea (cross-hatched areas where the tidal volume trace is substantially flat), which are common in sleeping canines, the ECG signal reflects purely the electrical activity of the myocardial muscle absent the impact of transient transmural pressure gradients associated with breathing. As seen in FIG. 4A, and in more detail in FIG. 4B, the animal's heart rate during these apneic periods is very stable and its ECG is constant. It is also worth noting the variability in the animal's heart rate prior to these apneic periods, such variability associated with the animal's breathing cycle and resulting in beat-to-beat differences in ECG. This is known as respiratory sinus arrhythmia (RSA).

Example 3

Continuous monitoring of non-human animals primates (NHP), enables identification of behavioral and activity patterns that indicate when such an animal may be agitated or experiencing stress. For example, such patterns may indicate that an animal, which was once previously thriving in the environment with other animals, is beginning to manifest negative behavior that could result in their removal from a research colony. This inappropriate behavior is broadly termed 'stereotypical' behavior, and ranges from repetitive movements to obsessive behaviors, and at the extreme, severe self-injurious behavior. Animals who display stereotypical behaviors are not effective for research and are typically removed from the cohort of available animals. Moreover, if they don't positively respond to environmental and stimuli changes, they cannot be further used for research in the future.

Physiological data collected with the monitoring garment of FIG. 3C can identify abnormal movement patterns as well as the presence of repetitive/obsessive type behaviors in non-human animals. For example, FIGS. 5A and 5B illustrate normal and abnormal, respectively, activity and rest patterns on an animal over a period of over 20 hours.

Figure 5A:
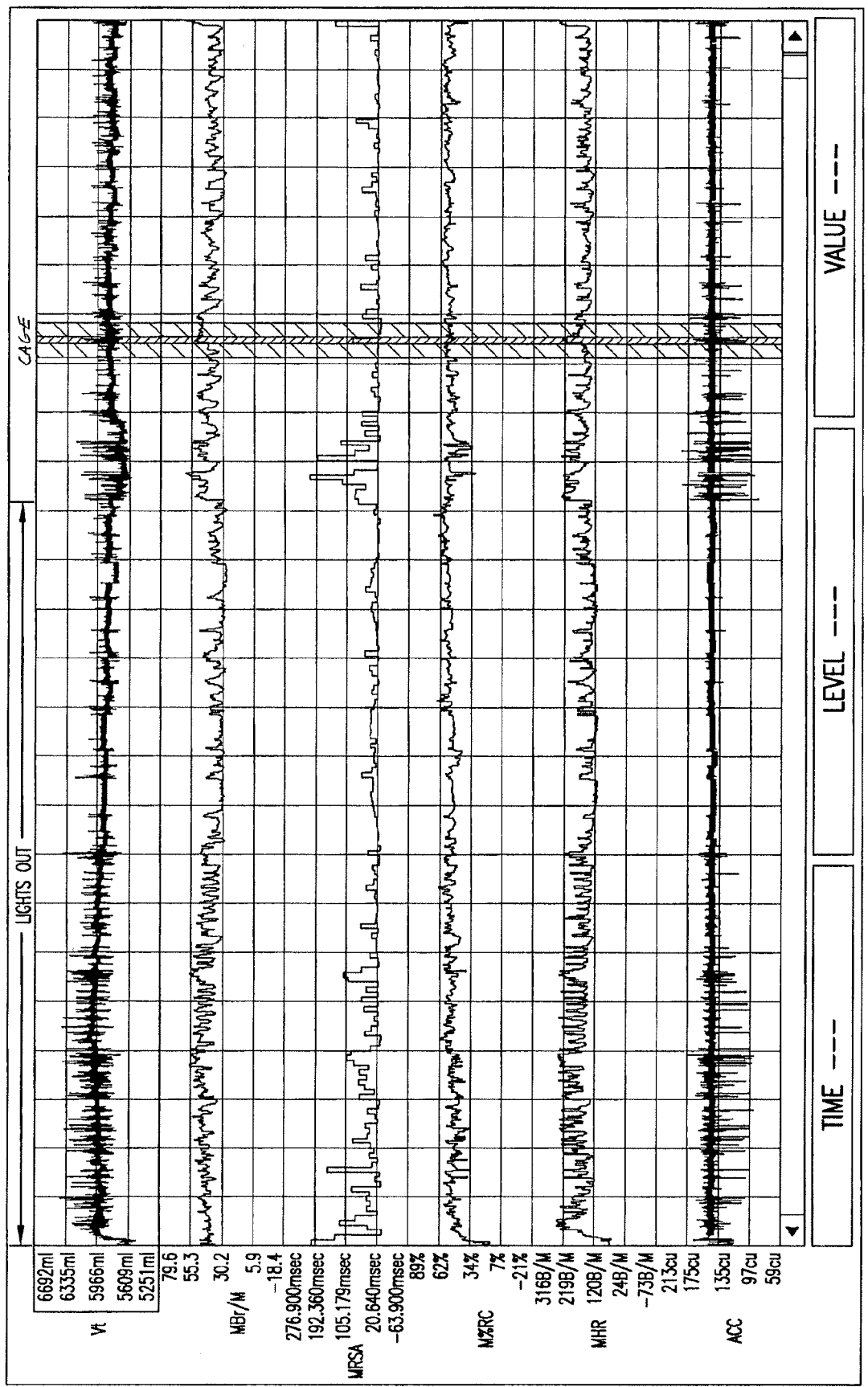
FIGS. 5A-B illustrate exemplary monitoring data.

In FIG. 5A, the overnight, "Lights Out" period is about 12 hours in length. The first half contains multiple discreet bouts of activity and rest as identified in the ACC trace, the Vt trace, the median breath rate (mBr/M) trace, and the median heart rate (MHR) trace. Later in the night, the animal appears to rest quietly for approx. 6 hrs (identified in the ACC, Vt, mBr/M, and MHR traces). During the Lights On period, there are distinct periods of activity with intervals of rest. The cross-hatched "Cage" period during the Lights On period is when cage cleaning occurred in primate room, and the narrower cross-hatched period within the Cage period is when the monkey's own cage was being cleaned.

Figure 5B:
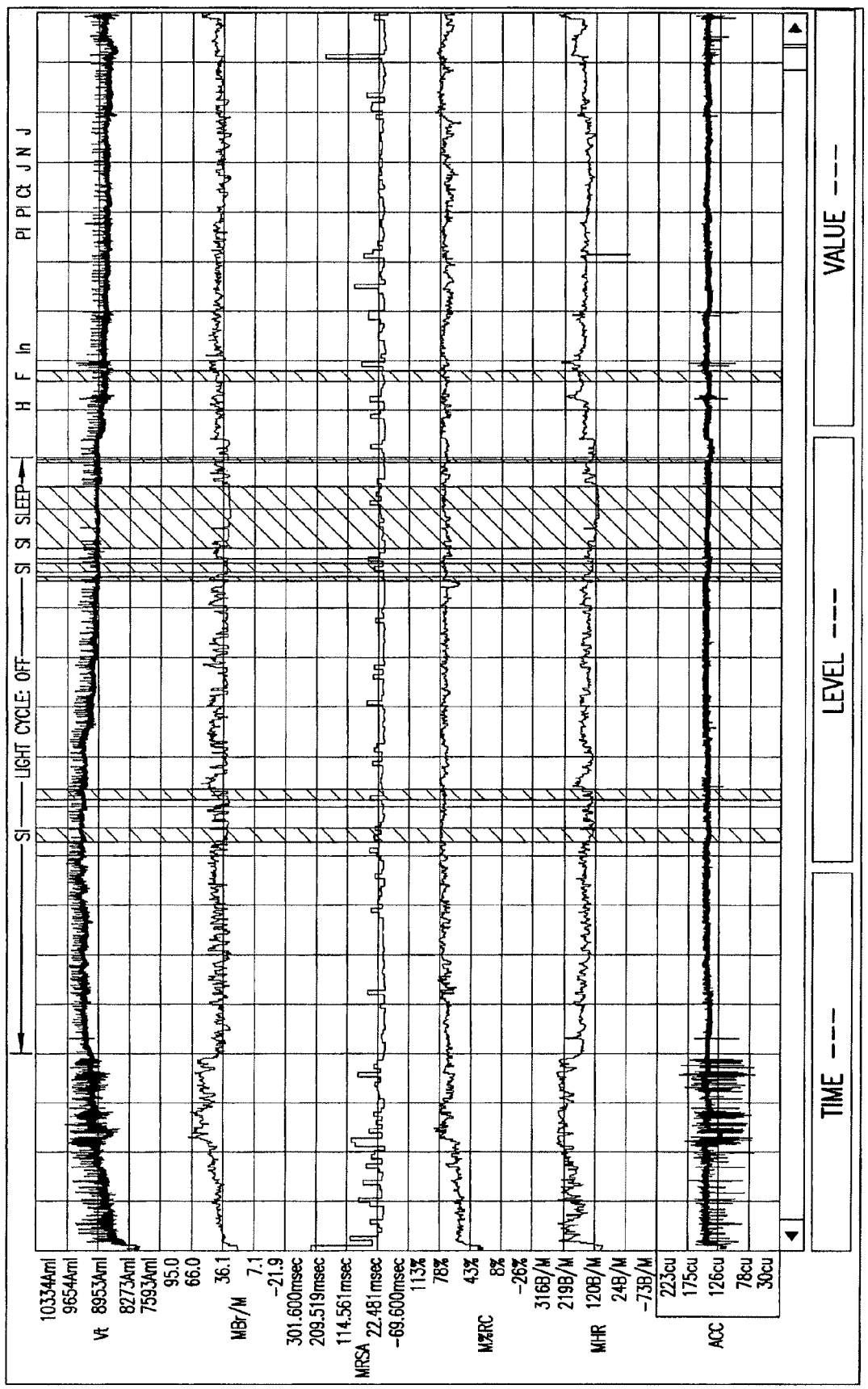

In FIG. 5B, the overnight, "Light Cycle: Off" period is also 12 hours in length. During this time, the animal's activity is reduced, but there does not appear to be any quite rest intervals compared to the data of FIG. 5A. The animal exhibits constant movement throughout the night, as shown in the ACC trace, as well as unstable physiological conditions, as shown in the Vt, mBr/M, and MHR traces. Towards the end of the Lights Off period, there is about 50 min period of quiet rest. During the wake period before Lights Off, the animal is extremely active. When the lights come back on, the animal's activity shows very little difference compared to the previous 12 hours (i.e., overnight).

Figure 6A:
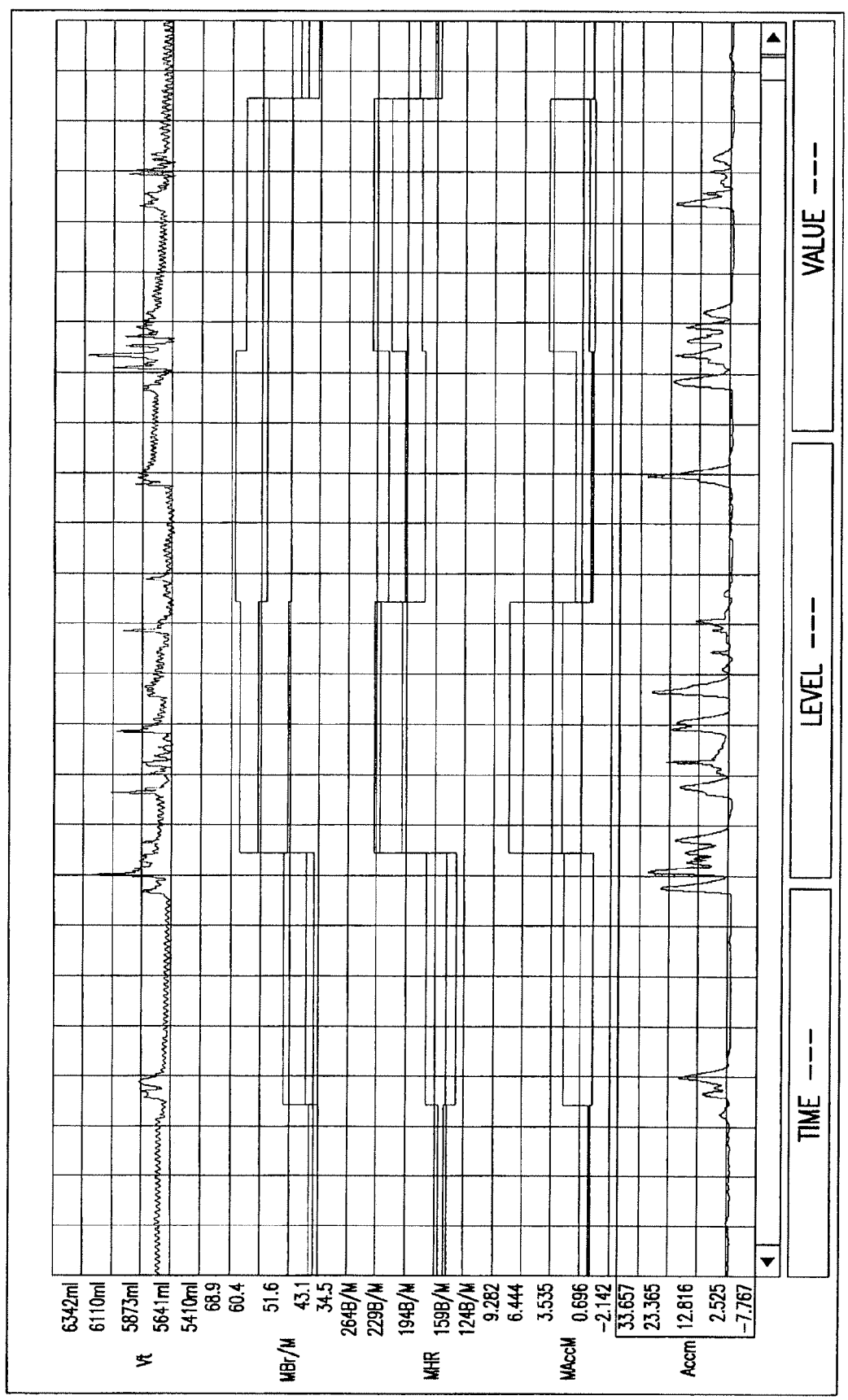
FIGS. 6A-B illustrate exemplary monitoring data.
Figure 6B:
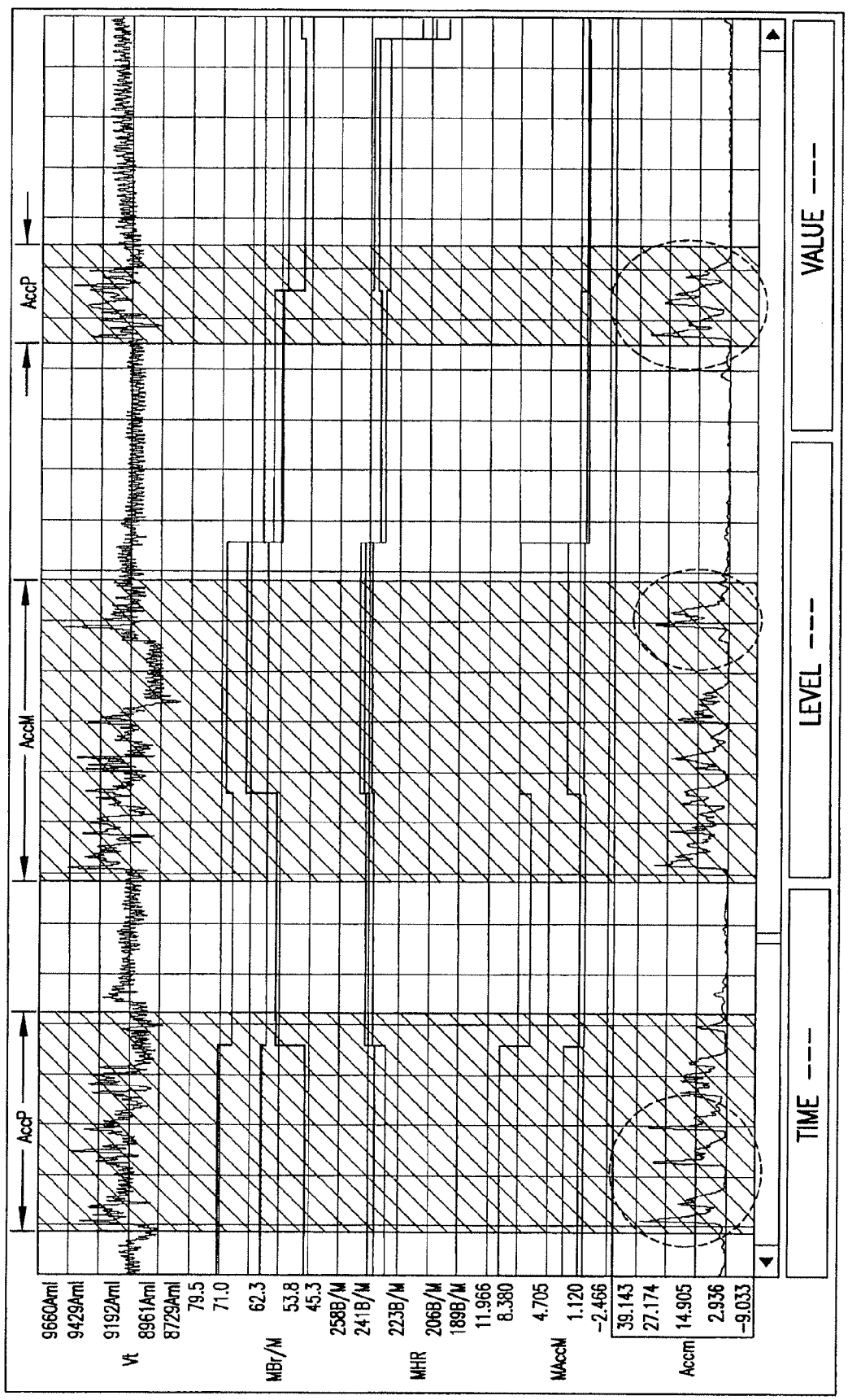

FIG. 6A illustrates the physiological data of a healthy animal collected over a period of 5 minutes. As seen in the median accelerometer trace (AccM), the animal exhibits a normal pattern of activity that is typically irregular in pattern and timing. Comparing FIG. 6A with the 5 minute activity trace of FIG. 6B of an animal displaying stereotypical behavior, it is clear from the circled portions that the animal exhibits a series of repetitive, bi-phasic movements that is indicative of such abnormal behavior.

Figure 7A:
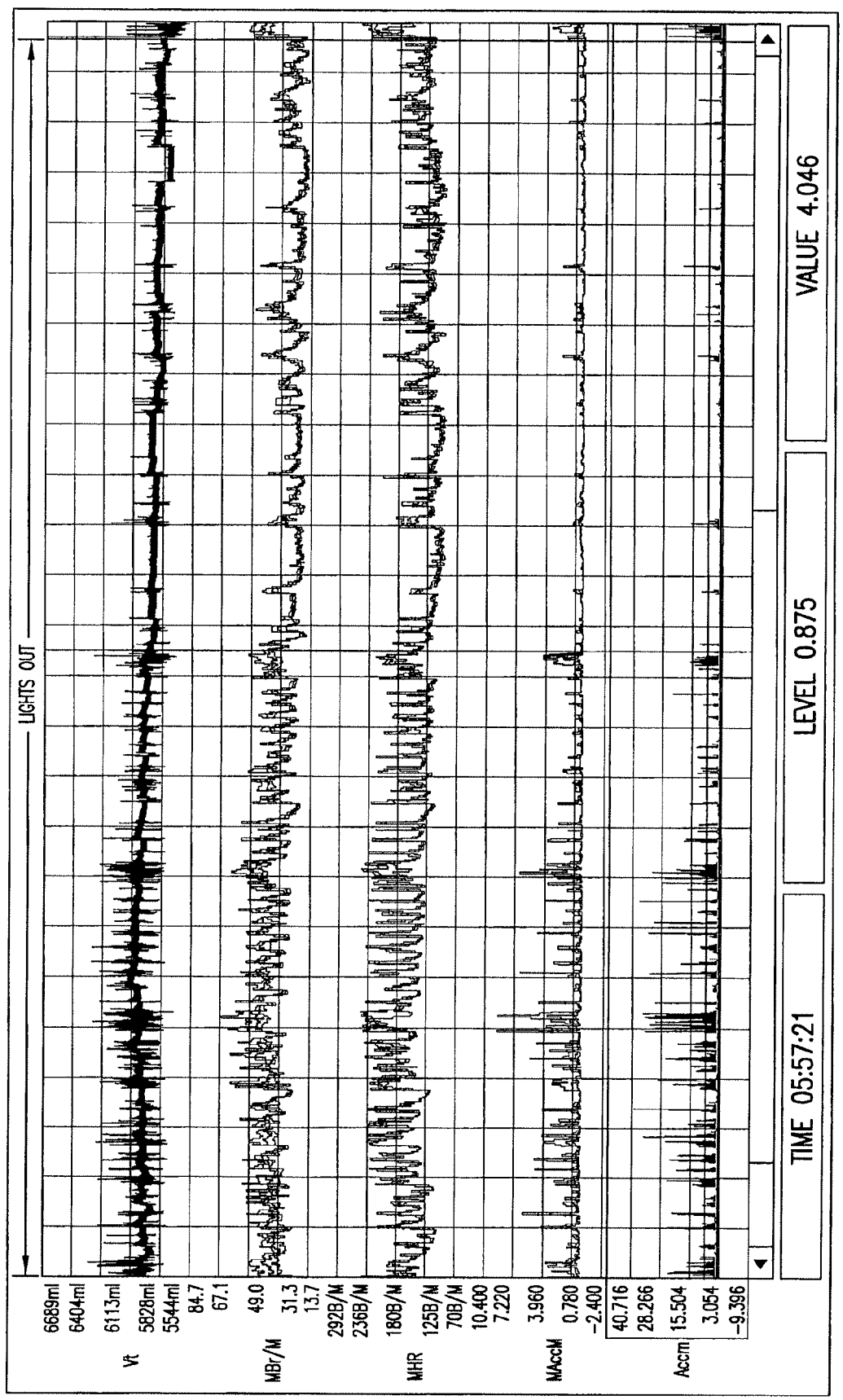
FIGS. 7A-B illustrate exemplary monitoring data.
Figure 7B:
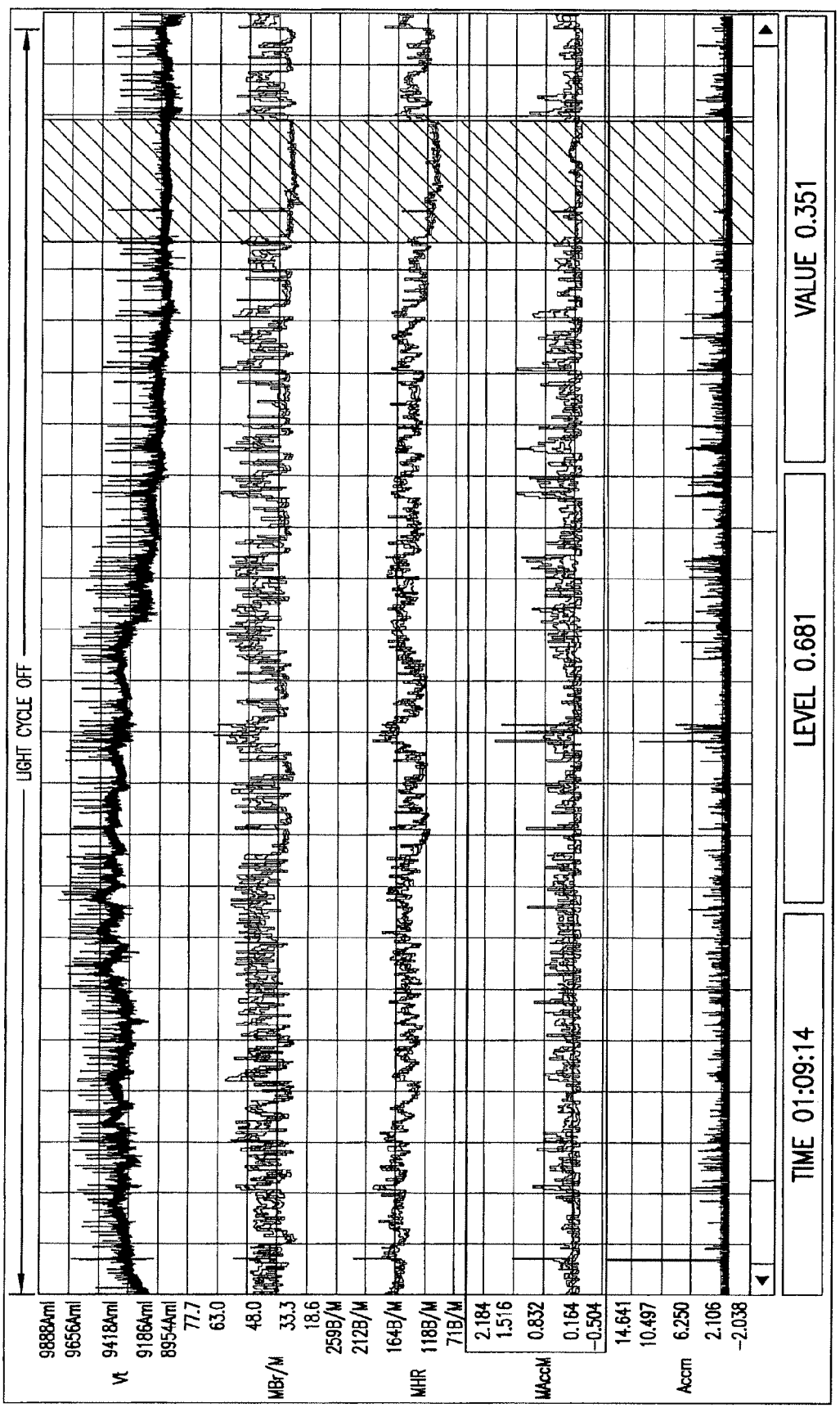

FIGS. 7A and 7B show another example of the physiological data that is indicative of stereotypical behavior. In FIG. 7A, the animal displays normal intervals of activity, followed by relatively long periods of rest after lights are turned out in the environment. The animal appears to rest physiologically for almost 6 hours during the entire 12 hour Lights Out cycle (i.e., the rest period is shown from about the middle of the trace all the way to the end of the Lights Out period). The animal also exhibits distinct intervals of activity and rest in the period before quieting down.

In contrast, FIG. 7B shows the physiological data of an animal displaying stereotypical behavior, characterized in a constant level of activity long into the Lights Out period with relatively little rest. The animal only gets about 60 minutes of physiological rest (cross-hatched period). During this time, the respiratory tidal volume trace, breathing frequency, and heart rate stabilize, and the median accelerometer trace shows very little movement. When the animal wakes, however, all of the traces regain their previous characteristics. Such physiological data may also correlate fairly well with, or can be used to identify the presence and/or change in the degree of physiologic stress experienced by the animal.

As shown in the data provided in FIGS. 7A and 7B, a garment substantially similar to that illustrated in FIGS. 2A-E can also be used to infer sleep time and/or periods of quiet physiologic rest using variability and absolute level of various physiologic data streams. This data can provide valuable information for improving animal care and husbandry, for example, in veterinary environments. An examination of the stability of respiratory frequency and volume can discriminate periods of sleep or 'physiologic rest' in animal species. Distinct physiologic states can be discriminated which are similar to the patterns of sleep and wakefulness in humans. Physiologic rest can be observed in low activity levels, heart rate, and breathing frequency, concurrent with reduced variability in breathing frequency, tidal volume, and heart rate. Within periods of 'physiologic rest' respiratory patterns specific to various diseases and disease models can be identified, such as sleep apnea (below) and Cheyne-Stokes respiration in models of congestive heart failure, among others.

Example 4

Periods of emesis in canines, felines, can often be automatically recognized in the absence of visual observation of the animal by finding characteristic patterns of changes in abdominal and rib cage sizes, girths, or volumes. These are preferably monitored using the above described monitoring garment and associated apparatus. These characteristics patterns result from an initial period of retching following by actual expulsion of stomach contents. Often, the retching is preceded by a brief panting-like prodrome. Periods of emesis can be similarly recognized in other carnivores, and more generally other quadrupeds or animals, which retch prior to expulsion. Whether or not a particular species displays such characteristic patents can be readily ascertained by observation of one to a few periods of emesis. Thus, it is without limitation that the following description is largely in terms of emesis in canines such as dogs.

In the following, the term "period of emesis" is taken to refer to all changes from an initial, normal respiratory pattern, through actual expulsion of stomach contents, and back to a normal respiratory pattern. "Retching" is taken to refer to abdominal contractions without expulsion of stomach contents (because, e.g., the glottis being closed). "Vomiting" is taken to refer to the actual expulsion of stomach contents. And "prodrome" is taken to refer a period in which the respiratory pattern changes prior to retching. Further, respiratory "volumes" (also referred to herein as "gross" motions) are taken to refer to a short term average of an externally measurable size (which vary with internal volumes) of a body compartment averaged over a short time period, e.g., rib cage (RC) or abdominal (AB) sizes averaged over several breaths, e.g., average over 20 to 60 sec, while respiratory "amplitudes" (also referred to herein as "fine" motions) are taken to refer to differences in respiratory volumes (and indirectly volumes) during a single breath, e.g., the difference in RC or AB size between the beginning of an inspiration and the end of the inspiration.

Figure 8A:
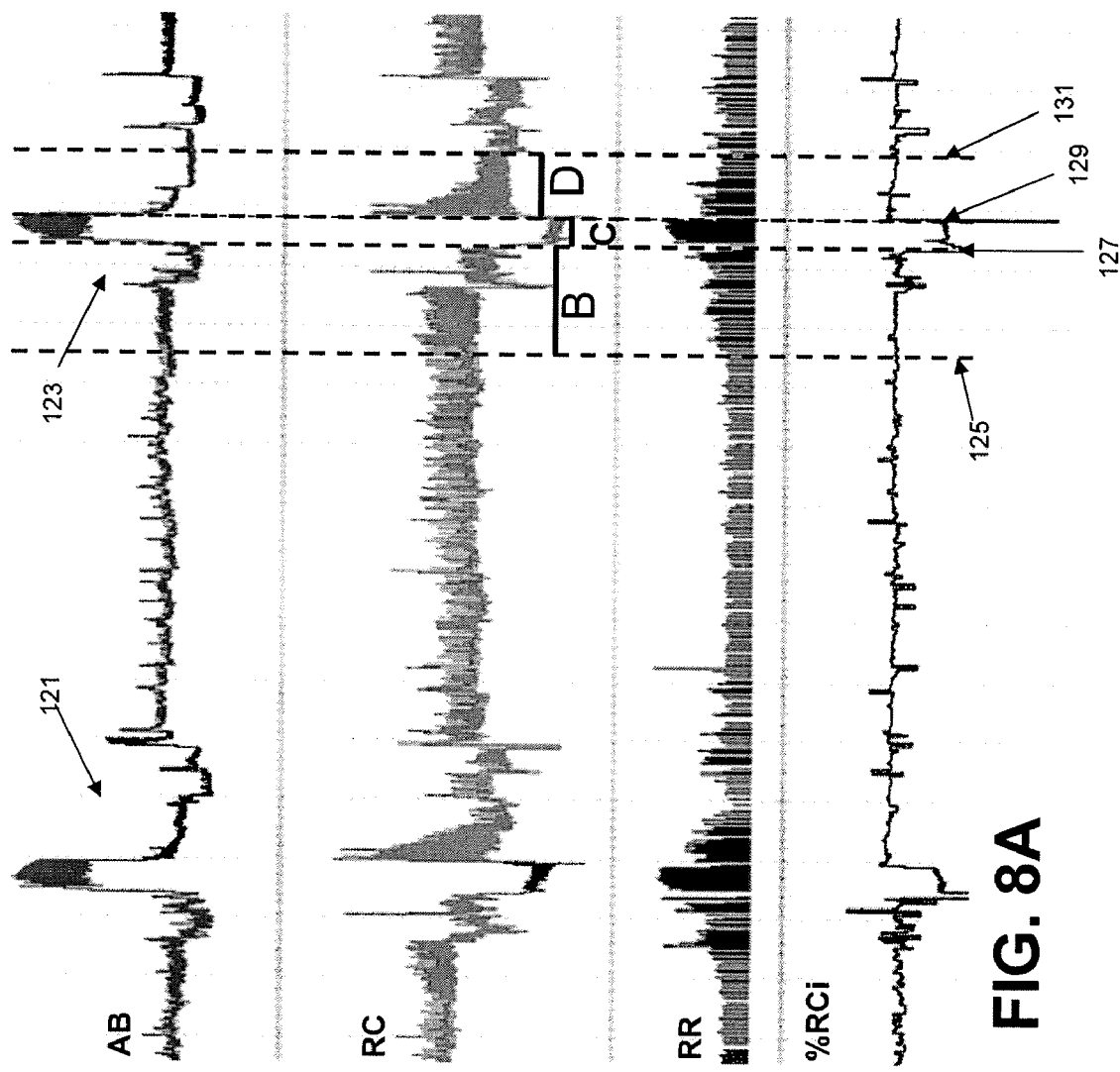

FIGS. 8A-8C illustrate data from periods of emesis in a medium weight dog obtained from a dog using a monitoring garment similar to that illustrated in FIG. 4C and displaying the characteristic patterns by which the present invention can recognize emesis. In these figures, traces labeled "RC" illustrate rib-cage volumes versus time; traces labeled "AB" illustrate abdominal volumes versus time; traces labeled "RR" illustrate respiration rates versus time; and traces labeled "% RCI" illustrate the time variation of the percentage inspiratory rib-cage volume changes are of inspiratory tidal volumes (that is the rib cage volume change during inspiration divided by the tidal volume during inspiration).

First, FIG. 8A illustrates in a compressed fashion an approximately 7-8 min. window during which occur two periods of emesis 121 and 123 with the characteristic patterns. Particular times during second period 123 are marked for convenience of discussion by vertical dashed lines 125, 127, 129, and 131 which demarcate periods B, C, and D, respectively. In general, periods C and D present the stereotypical pattern that is principally characteristic of periods of emesis, while period B is a prodrome, which may not present in all cases, and when present, can have variable characteristics. In detail, as can be appreciated from FIG. 8A, prodrome B, when present, is grossly characterized and recognized by changes in respiratory patterns from a prior baseline that persist for 10 s of secs. In particular, these changes can include an increase in RR (up to two times the baseline RR) along with either or both of variable decreases in RC volumes below their preceding baseline and increases in RC respiratory amplitudes. AB respiratory amplitudes typically vary along with the RC amplitudes during this period so that % RCi is largely unchanged. The increase in RR can be recognized by increases in the dominant frequency of RC and AB motions. This period begins gradually at approximately time 125 when the RR first begin to increase, but ends abruptly at time 127 when subsequent period C begins. Briefly, period B appears to an observer as a period of increasing panting which precedes the actual expulsion of abdominal contents.

Times before the beginning of period B, that is time of normal (no period of emesis) respiratory patterns, are also useful in this invention in that they establish baselines in respiratory parameters including RC and AB volumes and amplitudes, RR, and the like. Baseline values can be determined in various ways, e.g., by running averages, or preferably, by windowed median filtering.

Vomiting occurs next during periods C, a period of retching, and D, actual vomiting. Characteristic of period C is the significant increase in AB volumes above their recent baselines that is constant over a period of several seconds. Coincident with this increase in AB volumes is a significantly decrease in RC volumes below their recent baselines that also is constant over the same several second period. Both the volume changes occur abruptly over perhaps 1 to 5 breaths. These oppositely directed changed in AB and RC volumes are referred to herein as a "paradoxical motion", and specifically, since these relative volume changes are average over several breaths, the paradoxical motion is referred to herein as "grossly paradoxical". Also characteristic of the period is a significant increase in AB respiratory amplitudes by factors of at least about 2 and up to about 5 or more coincident with a significant decrease of RC respiratory amplitudes by factors of at least 2. A significant decrease in % RCi values reflects these changes in AB and AC amplitudes. Finally, RR along with dominant frequencies of AB and RC motions continues to increase, and can reach a level of more than twice baseline. As noted period C begins after period B with the above abrupt changes at time 127, and ends at time 129 with the equally abrupt partial reversal of the prior changes and return towards baselines. Briefly, period C appears as a period of retching, that is a period of intense abdominal contractions against a compressed rib cage and closed glottis. Stomach contents are urged out of the abdomen but cannot be yet expelled.

Finally, vomiting occurs at the transition between periods C and D and can occasionally continue into period D. At this transition and into period D, the AB and RC expansions and contractions occur in a manner that permits stomach contents to be expelled through the more relaxed rib cage and open glottis. Characteristic changes in respiratory patterns include abrupt reversal of the majority of the changes in RC and AB volumes that characterized period C within at most a few breaths of time 129, the beginning of period D. The remainder of the volume changes decay during the course of period D. The respiratory amplitudes also display characteristic changes. The AB amplitudes decrease abruptly, along with the AB volumes, to substantially baseline values. The RC amplitudes increase equally abruptly to values significantly above baseline, and decay back to baseline over the course of period D. Reflecting the changes in respiratory amplitudes, % RCi rapidly returns to a level that somewhat amount above baseline, and also decays back to baseline over the course of period D. The RR also decays over the course D to approximately the baseline RR values prevailing before the period of emesis. Period D ends gradually approximately at time 131 as normal respiratory patterns resume.

The timings of these periods are variable between different species, and between different individuals within a single species, and can be variable even for a single individual. Typical timings for dogs of medium build are: period B—approximately 45 sec.; period C—approximately 15 sec.; period D—approximately 30 sec.; with variations in these timings between approximately −50% and approximately +150%.

Further features characterizing periods of emesis can be discerned in higher resolution presentations of respiratory monitoring data as in FIG. 8B, where the trace labeled "RA EMG" is an EMG (electromyogram) of the rectus abdominus muscle (which is active in abdominal contractions such as sit-ups and the like). This figure illustrates a period of emesis including the final portion of prodrome period B, the entire period C, and the initial portion of period D. Dashed lines 141 and 143 mark times that correspond to times marked by lines 127 and 129, respectively, in FIG. 8A. Specifically line 141 marks the beginning actual vomiting episode, and line 145 marks the single vomiting occurrence of the episode (in other episodes there can be two or more occurrences of vomiting). The previously-discussed overall paradoxical motion of the AB and RC volumes is clearly apparent also at this resolution.

However, examining FIG. 8B in detail, it can be seen that the RC and AB volumes also tend to move in a paradoxical manner on a breath by breath basis (referred to herein as "finely paradoxical"). Specifically, shortly in advance of vomiting, when the RC and AB motions are grossly paradoxical, these motions are also finely paradoxical, while after vomiting, when the RC and AB volumes and motions have normalized and are no longer grossly paradoxical, these motions tend to be coincident and are no longer finely paradoxical. For example, examining this data at the time indicated by line 143, it can be seen that the AB volume is at or near a local (in time) minimum, while the RC volume is at or near a local maximum. Further, shortly before or after this time, the RC and AB motions are in opposite directions. And examining this data are the time indicated by line 147, it can be seen that the RC volume is near a local maximum while the AB volume is approaching a local maximum. Such coincident motion also characterizes normal breathing. Generally, it has been found that, before vomiting, the RC and AB motions approximately 180° out of phase usually within ±45°.

FIG. 8B also records contractions of the rectus abdominus muscle near the times AB volume minima. These contractions are a specific manifestation of the retching that occurs prior to actual vomiting. Here approximately 20-25 retching episodes precedes a single actual vomiting episode.

FIG. 8C confirms these characteristics and expands on them. This figure illustrates a portion of a period of emesis including the final portion of period C and the initial portion of period D (which correspond to the similarly identified periods in the prior figures). Actual vomiting occurs about the time indicated by line 151 at the transition between periods C and D. Again, during the terminal portion of period C, the AB and RC motions tend to be finely paradoxical. For example, at the time indicated by line 153, the RC volume near a local maximum and the AB volume near a local minimum. In contrast, at the beginning and throughout period D, the AB and RC motions tend to be coincidence. For example, at the time indicated by line 155, both the AB and RC volume near local maxima.

FIG. 8C also illustrates further measures that can be use to quantitatively characterize to above-described characteristic of periods of emesis. The series of values labeled as ViVolRC is the inspiratory RC volume, that is the volume difference between beginning and end inspiration. These values indicate period C by decreased volumes; they indicate period D by increased volumes; and they indicate the transition between these periods by a transition between decreased and increased volumes occurring within one to two (up to five) breaths. The series of values trace labeled as ViVolAB is the similarly-defined inspiratory AB volume. Conversely, these values indicate period C by increased volumes; they indicate period D by decreased volumes; and they indicate the transition between these periods by a transition between increased and decreased volumes occurring within two to three (up to six) breaths.

The trace labeled as SViVolRC is a running average of the median of ViVolRC values over 12 sec window. This trace reflects the ViVolRC values and is characteristically depressed in period C, characteristically elevated in period D, and characteristically increasing through the transition between periods C and D by a decrease at a rate reflecting the effects of averaging and taking the median. Similarly, the trace labeled as SViVolRAB is a running average of the median of ViVolAB values over 12 sec window. This trace reflects the ViVolAB values and is characteristically elevated in period C, characteristically depressed in period D, and characteristically decreasing through the transition between periods C and D by a decrease at a rate reflecting the effects of averaging and taking the median. The trace labeled as SViVolABRC is the ratio of SViVolABM to SViVolRCM. Its shape directly reflects the shape of the constituent traces, SViVolABM, and SViVolRCM.

The trace labeled as STFTABF is a short time Fourier transform of AB over 20 sec periods and reflects the dominant frequency in the AB volume signal. This traces reflects the previously discussed behavior of this dominant frequency (which indirectly reflects the RR): elevated in period C; depressed in period D; and decreasing across the transition between periods C and D at a rate reflecting the 20 sec width of the window.

All the above described characteristics, the gross and fine behaviors of the RC and AB volumes and the several quantitative parameters, can be used singly on in combination to recognized periods of emesis. Preferably, at least the gross behavior of the RC and AB volumes is used, and is combined with other characteristics to achieve increased certainty.

Example 4

Bark and cough can be recognized in canines and seals, and in other animals that make communicative vocalizations that are sharp auditory expulsions, by finding characteristic patterns of changes in abdominal and rib cage sizes, girths, or volumes that occur along with sound above a threshold level. These are preferably monitored using the above described monitoring garment and associated apparatus including RC and AB IP bands and a microphone, e.g. a throat microphone. Barks and coughs can be characterized and recognized by the pattern of the respiration occurring in conjunction with the vocalization; and optionally, different types of barks, e.g., a bark, a yelp, and so forth, can be characterized and recognized by the average pitch of the vocalization. The following description is largely in terms of emesis in canines such as dogs, although it should be understood that the invention is applicable to other barking species.

Vocalizations such a sound events from a canine, or other barking animal, are preferably recorded with a throat microphone. Analysis of sound events can, for simplicity, be adapted from sound event analysis adapted to humans. Such analysis is described in U.S. Pat. No. 7,207,948, issued Apr. 4, 2007, which is incorporated herein in its entirety for all purposes. Briefly, in order to determine the presence of sound events, sound can be preferably sampled at a higher rate, e.g., about 1500 Hz, and then is effectively smoothed by being down sampled to a lower rate, e.g., about 50 Hz. The amplitude of, or energy in, the thereby smoothed sound signal is then preferably thresholded to determine events. An event (recorded in the EVT trace in FIGS. 9 and 10) occurs when the threshold is exceeded and continues until the threshold is no longer exceeded. Events with a length less than a threshold (e.g., 100 msec.) can be discarded as likely to be artifact. A preferred method to determine pitch is cepstrum analysis. Sounds for pitch analysis are preferably of higher quality, e.g., being samples at 8 hHz or greater with an accuracy of 8 bits or greater. Briefly, cepstrum analyzes such sound to determine sound energy versus a logarithmic frequency scale which is chosen to model the auditory sensitivity and discrimination of the animal or human. It can return an indication of a dominant pitch of an animal vocalization.

Figure 9:
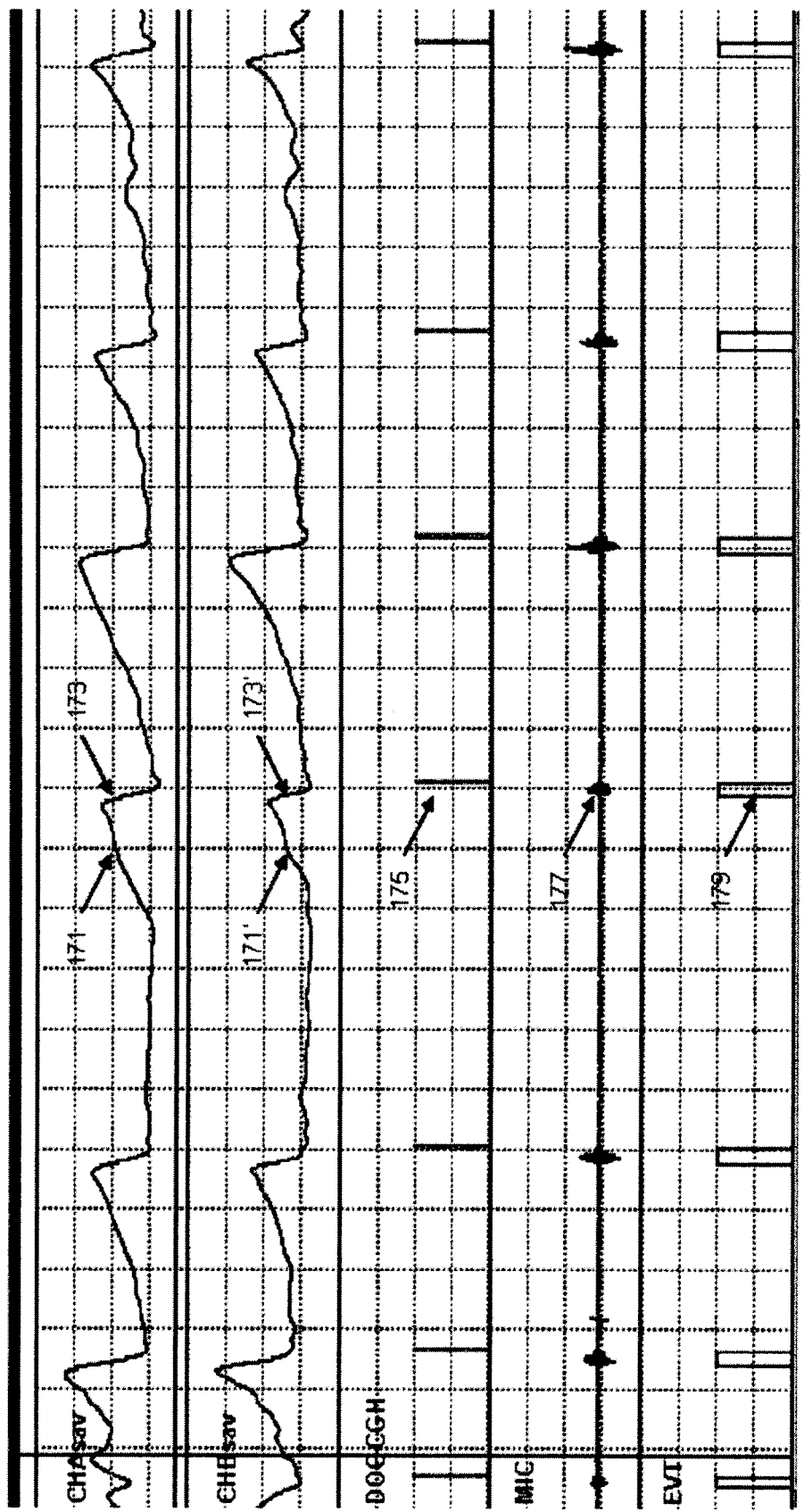
FIG. 9 illustrates exemplary monitoring data obtained from a canine.

FIG. 9 illustrates data taken during a series of typical coughs in a medium sized dog. The illustrated coughs are spaced between about 0.7 sec and about 1.5 sec. Sound recorded from a throat, which is illustrated in FIG. 9 as the trace labeled as MIC, is analyzed (including thresholding) as described above to determine the presence and length of sound events, which is in turn illustrated as trace labeled EVT. CHAsav and CHBsav are two channels of size signals with CHAsav being primarily sensitive to RC sizes and CHBsav being primarily sensitive to AB sizes. These channels have been filtered to remove noise and certain artifacts by a filter the nevertheless preserves the shapes of rapid motions. A polynomial, Savitsky-Golay smoothing filter is preferred.

As illustrated, the breath during which dog cough occurs is characterized by longer inspiratory period, e.g., periods 171 and 171' in each of the channels, with a correspondingly lower and approximately constant inspiratory rate followed by a considerable shorter expiratory period, e.g., periods 173 and 173' in each of the channels, with a correspondingly higher approximately constant expiratory rate. In the illustrated example, the inspiratory time is longer, in almost all cases longer than about 0.5 sec and usually about 1.0 sec, while the expiratory time is shorter, in all cases shorter than about 0.2 sec and usually about 0.1 sec. Thus, the inspiratory time can be from about 2 times, to about 5 times, to about 10 and higher times longer than the expiratory time. The animal's vocalization, e.g., sound 177, occurs during the short expiration and is correspondingly short, occupies a correspondingly small fraction (less than about 10%) of breath time, and has an amplitude generally lower than vocalization during barks or yelps. Event 179 marks the location and duration of sound 177.

Following from these inspiratory and expiratory characteristics, the breath waveform has a saw tooth shape that is characteristic. Dog coughs also usually occur in series and not as isolated single events, so dog coughs appears as a series of such sawtooths. Here, the coughs are spaced by about between 0.7 sec and 1.5 sec. Dog coughs can be automatically recognized by some or all of these characteristics, preferably the inspiratory and expiratory times and their ratio. Recognition reliability can be increased by also considering inspiratory and expiratory flow rates, breath waveform shape, and vocalization duration, amplitude, and position with respect to the accompanying breath. The trace labeled as DOGCOUGH is the output of an automatic recognition process providing time of recognized coughs, e.g., recognized cough 175. The method evaluates the above characteristics to determine cough occurrence.

Figure 10:
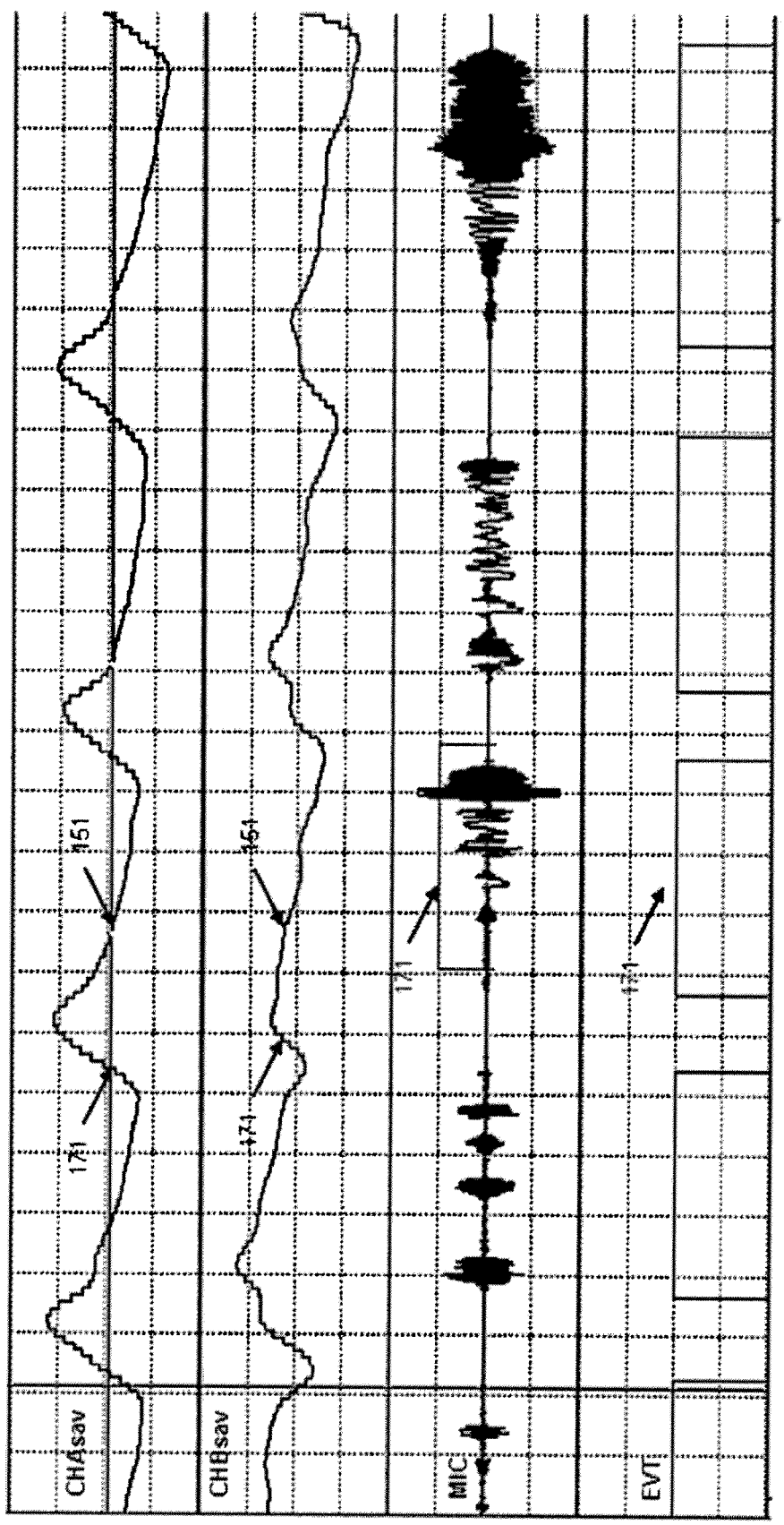
FIG. 10 illustrates exemplary monitoring data obtained from a canine.

FIG. 10 illustrates data taken during a series of typical barks in a medium sized dog. The illustrated barks are about 0.7 sec. long and are spaced apart by about 1.3 sec. In this figure, the traces labeled as CHAsav, CHBsav, MIC, and EVT have the same meanings as in FIG. 9. It is apparent that many characteristics of dog bark are significantly and recognizably different than dog cough. First, the bark vocalization are longer in time, e.g., from about 0.5 sec up to about 1.0 sec or longer, have higher amplitude, and occupy a large fraction, e.g., from about 40% up to about 70% and higher of total breath time that do coughs. For example, bark 175 extends for about 65% of the total breath time, the breath extending from a beginning at the time indicated by line 179 and to an ending at the end of bark 175. Event 177 marks the location and duration of this sound event. Further, the bark amplitude, especially near the end of the bark, is large compared to cough amplitude. Barks generally occur on expiration.

Second, the breath waveform during a bark is different from the breath waveform during a cough. The inspiration, e.g., inspiration 171 and 171' in each of the channels, occupies approximately half of the time between barks while the initial part of expiration, e.g., expiration 173 and 173' in each of the channels, occupies that letter half of the period. During this period, the inspiration and expiration rates are approximately constant and approximately equal. However, the inspiration rate can occasionally be somewhat larger than the expiration rate. As a result of these characteristics, the breath waveform in the periods between barks is approximately symmetrical with a maximum near or at the middle of this period. For example, inspirations 171 and 171' and expirations 173 and 173' are all about 0.15 sec. However, bark occurs during the final period of expiration and accordingly the final period of expiration, e.g., expiration periods 183 and 183' in each of the channels, is extended for a longer period of time than the initial period and is necessarily at a lower rate. Here, the final period of the expiration extends for about 0.7 sec, and is thus about 4 times longer than the initial period. Generally, the final period can be from about 2 times to about 4 and higher times longer than the initial periods. The total expiration period can therefore be from about 3 times to about 5 and higher time longer than the total inspiration period.

Dog coughs can be automatically recognized by some or all of these characteristics, preferably the ratio of total inspiration times to total expiration times and by the vocalization amplitude. Recognition reliability can be increased by also considering inspiratory and expiratory flow rates, breath waveform shape between barks, and the two periods of expiration.

Bark-like vocalization can occur in various forms, for example, as regular barks, as yelps, and howls, as whines, and the like. These forms can be distinguished based on pitch analysis. First, bark-like vocalizations are recognized as described above. Then, bark-like vocalizations with a generally lower pitch are classified as regular barks; bark-like vocalizations with a generally higher pitch are classified as whines; bark-like vocalizations with a generally intermediate pitch are classified as yelps; and bark-like vocalizations with a generally rising pitch are classified as howls. The levels of lower pitch, intermediate pitch, and higher pitch are preferably chosen based on the type and size of dog.

These examples demonstrate that the monitoring garments and systems of this invention obtain reliable monitoring data that can be processed and consistently interpreted to provide useful physiological and behavioral information on various species of animals.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which, if not previously incorporated by reference, are hereby explicitly incorporated herein, in their entirety, by reference for all purposes. Further, none of these references, regardless of how characterized above, is admitted as prior to the invention of the subject matter claimed herein. Headings are used hereon for clarity and convenience only and without any intended limitation.

What is claimed is:

1. A method of identifying emesis in an animal comprising the steps of:
   receiving monitoring data from the animal, said monitoring data comprising signals reflecting abdominal (AB) dimensions and signals reflecting rib cage (RC) dimensions, said AB and RC signals varying with respiratory motions;
   determining a characteristic pattern in said AB and RC signals using a processor, said characteristic pattern comprising
   an increase in an average AB dimension from a baseline AB dimension and a decrease in an average RC dimension from a baseline RC dimension, the increase and decrease occurring abruptly within a few breaths and persisting for several breaths,
   a decrease in said average AB dimension towards said baseline AB dimension and an increase in said average RC dimension towards said baseline RC dimension, said RC dimension increase and said AB dimension decrease occurring within five (5) breaths, and
   one or more synchronous breath induced changes in AB and RC dimensions, the amplitude RC dimension change being greater than a baseline RC dimension; and
   identifying a period of emesis when said characteristic pattern is determined.

2. The method of claim 1, wherein said increase in average AB dimension and said decrease in average RC dimension occurs within five (5) breaths, and wherein said RC and AB dimension changes persist for at least ten (10) breaths.

3. A method of identifying cough in an animal comprising the steps of:
   receiving monitoring data from the animal, said monitoring data comprising signals reflecting abdominal (AB) dimensions and signals reflecting rib cage (RC) dimensions, said AB and RC signals varying with respiratory motions, and signals reflecting vocalizations;
   determining a characteristic pattern in said AB, RC and vocalization signals using a processor, said characteristic pattern comprising
   an inspiratory period with a steady inspiration rate and lasting for a first period of time,
   an expiratory period with a steady expiratory rate and lasting for a second period of time, wherein said inspiratory first period of time is greater than said expiratory second period of time and said inspiratory rate is lower than said expiratory rate,
   determining a ratio of said inspiratory time to said expiratory time;
   a vocalization occurring during expiration; and
   identifying a cough event when said characteristic pattern is determined.

4. The method of claim 3 wherein said ratio of said inspiratory time to said expiratory time is at least 2.

5. A method of identifying bark in a barking animal comprising the steps of:
   receiving monitoring data from the animal, said monitoring data comprising signals reflecting abdominal (AB) dimensions and signals reflecting rib cage (RC) dimensions, said AB and RC signals varying with respiratory motions, and signals reflecting vocalizations;
   determining a characteristic pattern in said AB, RC and vocalization signals using a processor, said characteristic pattern comprising
   an inspiratory period with a steady inspiration rate and lasting for a first period of time,
   an expiratory period lasting for a second period of time, wherein said expiratory second period of time is greater than said inspiratory first period of time,
   determining a ratio of said inspiratory time to said expiratory time;
   a vocalization occurring throughout expiration; and
   identifying a barking event when said characteristic pattern is determined.

6. The method of claim 5 wherein said ratio of said expiratory time to said inspiratory time is at least 3.

7. The method of claim 5 wherein said barking animal comprises a canine or a seal.

* * * * *